US011612707B2

(12) United States Patent
Peake et al.

(10) Patent No.: US 11,612,707 B2
(45) Date of Patent: *Mar. 28, 2023

(54) TWO-WAY COMMUNICATIONS IN A MEDICAL DEVICE

(71) Applicant: ResMed Pty Ltd, Bella Vista (AU)

(72) Inventors: Gregory Robert Peake, Sydney (AU); Nathan Zersee Liu, Sydney (AU); Sakeena De Souza, Sydney (AU); Andrew Weale, San Diego, CA (US); Peter James Dassos, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/559,864

(22) Filed: Dec. 22, 2021

(65) Prior Publication Data

US 2022/0111166 A1 Apr. 14, 2022

Related U.S. Application Data

(63) Continuation of application No. 16/875,728, filed on May 15, 2020.

(Continued)

(51) Int. Cl.
*A61M 16/00* (2006.01)
*A61M 16/06* (2006.01)
(Continued)

(52) U.S. Cl.
CPC ...... *A61M 16/024* (2017.08); *A61M 16/0003* (2014.02); *A61M 16/06* (2013.01);
(Continued)

(58) Field of Classification Search
CPC ............ A61M 16/024; A61M 16/0003; A61M 2205/3334; A61M 2202/0208;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

AU 2007317446 5/2008
AU 2007317447 5/2008
(Continued)

OTHER PUBLICATIONS

"Respiratory Physiology", by John B. West, Lippincott Williams & Wilkins, $9_{th}$ edition published 2012 (8 pages).
(Continued)

*Primary Examiner* — Timothy A Stanis
*Assistant Examiner* — Matthew R Moon
(74) *Attorney, Agent, or Firm* — Nixon & Vanderhye, P.C.

(57) ABSTRACT

A system for providing continuous positive air pressure therapy is provided. The system includes a flow generator, a sensor, and a computing device. The computing device is configured to control operation of the flow generator based on sensor data. The computing device is further configured to display, on a display device, one or more questions relating to demographic and/or subjective feedback; responsive to displaying the one or more questions, receive one or more inputs indicating answers to the one or more questions; transmit the answers to a remote processing system; receive, from the remote processing system, settings determined based on the transmitted answers; and adjust control settings of the system based on the received settings.

16 Claims, 16 Drawing Sheets

Related U.S. Application Data

(60) Provisional application No. 62/848,991, filed on May 16, 2019.

(51) Int. Cl.
*A61M 16/10* (2006.01)
*A61M 16/16* (2006.01)

(52) U.S. Cl.
CPC .......... *A61M 16/105* (2013.01); *A61M 16/16* (2013.01); *A61M 2202/0208* (2013.01); *A61M 2205/3334* (2013.01); *A61M 2205/3553* (2013.01); *A61M 2205/502* (2013.01); *A61M 2205/52* (2013.01)

(58) Field of Classification Search
CPC .......... A61M 16/16; A61M 2205/3553; A61M 2205/52; A61M 16/06; A61M 16/105; A61M 2205/502
See application file for complete search history.

(56) References Cited

U.S. PATENT DOCUMENTS

| | | |
|---|---|---|
| 6,168,563 B1 | 1/2001 | Brown |
| 6,532,959 B1 | 3/2003 | Berthon-Jones |
| 6,564,797 B1 | 5/2003 | Mechlenburg et al. |
| 6,581,594 B1 | 6/2003 | Drew et al. |
| 6,949,073 B2 | 9/2005 | Sarel |
| 7,051,735 B2 | 5/2006 | Mechlenburg et al. |
| 7,252,636 B2 | 8/2007 | Brown |
| 7,297,119 B2 | 11/2007 | Westbrook et al. |
| 7,310,668 B2 | 12/2007 | Brown |
| 7,516,192 B2 | 4/2009 | Brown |
| 7,533,171 B2 | 5/2009 | Brown |
| 7,717,112 B2 | 5/2010 | Sun et al. |
| 7,866,944 B2 | 1/2011 | Kenyon et al. |
| 7,921,186 B2 | 4/2011 | Brown |
| 7,941,323 B2 | 5/2011 | Brown |
| 8,042,537 B2 | 10/2011 | Mechlenburg et al. |
| 8,060,378 B2 | 11/2011 | Iliff |
| 8,140,663 B2 | 3/2012 | Brown |
| 8,335,992 B2 | 12/2012 | Skidmore et al. |
| 8,548,937 B2 | 10/2013 | Saigal et al. |
| 8,573,209 B2 | 11/2013 | Bathe et al. |
| 8,636,479 B2 | 1/2014 | Kenyon et al. |
| 8,638,014 B2 | 1/2014 | Sears et al. |
| 8,733,349 B2 | 5/2014 | Bath et al. |
| 8,924,878 B2 | 12/2014 | Palmer et al. |
| 9,076,315 B2 | 7/2015 | Landau et al. |
| 9,119,925 B2 | 9/2015 | Vandine et al. |
| 9,183,720 B2 | 11/2015 | Miladin et al. |
| 9,563,745 B2 | 2/2017 | Saigal et al. |
| 9,788,801 B2 | 10/2017 | Gerder-Kallisch |
| 9,814,850 B2 | 11/2017 | Paul |
| 9,872,965 B2 | 1/2018 | Baloa Welzien et al. |
| 10,115,482 B2 | 10/2018 | Leichner |
| 2003/0213489 A1 | 11/2003 | Mechlenburg et al. |
| 2005/0131273 A1 | 6/2005 | Asano |
| 2007/0000494 A1 | 1/2007 | Banner et al. |
| 2007/0095887 A1 | 5/2007 | Barbosa |
| 2008/0068638 A1* | 3/2008 | Yagi .................. G06F 16/93 358/1.14 |
| 2008/0114689 A1 | 5/2008 | Psynik |
| 2009/0038616 A1 | 2/2009 | Mulcahy et al. |
| 2009/0044808 A1 | 2/2009 | Guney et al. |
| 2009/0050156 A1 | 2/2009 | Ng et al. |
| 2009/0187121 A1 | 7/2009 | Evans |
| 2009/0205662 A1 | 8/2009 | Kwok |
| 2009/0293875 A1* | 12/2009 | Kwok .................. A61M 16/024 128/204.18 |
| 2010/0000534 A1 | 1/2010 | Kooij et al. |
| 2011/0203588 A1 | 8/2011 | Armitstead |
| 2012/0145153 A1* | 6/2012 | Bassin .............. A61M 16/0069 128/204.23 |
| 2013/0104898 A1 | 5/2013 | Berthon-Jones |
| 2013/0131574 A1 | 5/2013 | Cosentino |
| 2013/0199534 A1 | 8/2013 | Steinhauer et al. |
| 2014/0000604 A1 | 1/2014 | Steinhauer |
| 2015/0154380 A1 | 6/2015 | Duckworth et al. |
| 2016/0071432 A1 | 3/2016 | Kurowski et al. |
| 2016/0193437 A1 | 7/2016 | Bao |
| 2016/0256642 A1 | 9/2016 | Soysa |
| 2016/0270718 A1 | 9/2016 | Heneghan et al. |
| 2016/0275259 A1 | 9/2016 | Nolan et al. |
| 2017/0231528 A1 | 8/2017 | Nathan |
| 2017/0266408 A1 | 9/2017 | Giovannelli et al. |
| 2017/0300652 A1 | 10/2017 | Strobridge |
| 2017/0311879 A1 | 11/2017 | Armitstead |
| 2017/0332906 A1 | 11/2017 | Cribbs et al. |
| 2018/0014777 A1* | 1/2018 | Amir .................. A61M 35/003 |
| 2018/0015245 A1 | 1/2018 | Frame et al. |
| 2018/0041569 A1* | 2/2018 | Smadja .............. G06Q 30/0201 |
| 2018/0092571 A1 | 4/2018 | Wood et al. |
| 2018/0153440 A1 | 6/2018 | Lee et al. |
| 2018/0199882 A1 | 7/2018 | Klee |
| 2018/0315063 A1 | 11/2018 | Cheesman |
| 2018/0369522 A1 | 12/2018 | Bassin |
| 2019/0000349 A1 | 1/2019 | Narayan et al. |
| 2019/0000350 A1 | 1/2019 | Narayan et al. |
| 2019/0024043 A1 | 1/2019 | Roach |
| 2019/0189258 A1 | 1/2019 | Barrett |
| 2019/0148025 A1* | 5/2019 | Stone .................. A61B 5/0022 705/2 |
| 2020/0121873 A1 | 4/2020 | Hudson |
| 2020/0388131 A1 | 12/2020 | Ueda |

FOREIGN PATENT DOCUMENTS

| | | |
|---|---|---|
| AU | 2013244091 | 10/2013 |
| AU | 2018282279 | 1/2019 |
| EP | 1124526 | 8/2001 |
| EP | 2081485 | 7/2009 |
| EP | 2091410 | 8/2009 |
| EP | 2393422 | 12/2011 |
| EP | 2859485 | 4/2015 |
| EP | 3193997 | 7/2017 |
| EP | 3220300 | 9/2017 |
| WO | WO 98/004310 A1 | 2/1998 |
| WO | WO 98/034665 A1 | 8/1998 |
| WO | WO200018347 | 4/2000 |
| WO | WO 2000/078381 A1 | 12/2000 |
| WO | WO 2004/073778 A1 | 9/2004 |
| WO | WO 2005/063328 A1 | 7/2005 |
| WO | WO2005106758 | 11/2005 |
| WO | WO 2006/074513 A1 | 7/2006 |
| WO | WO 2006/130903 A1 | 12/2006 |
| WO | WO2007145948 | 12/2007 |
| WO | WO2008057951 | 5/2008 |
| WO | WO2008057952 | 5/2008 |
| WO | WO 2009/052560 A1 | 4/2009 |
| WO | WO2010091168 | 8/2010 |
| WO | WO 2010/135785 A1 | 12/2010 |
| WO | WO2012094008 | 7/2012 |
| WO | WO 2012/171072 A1 | 12/2012 |
| WO | WO 2013/020167 A1 | 2/2013 |
| WO | WO2013187776 | 12/2013 |
| WO | WO2015054134 | 4/2015 |
| WO | WO2015062897 | 5/2015 |
| WO | WO 2016/019292 | 2/2016 |
| WO | WO2016039950 | 3/2016 |
| WO | WO2016042522 | 3/2016 |
| WO | WO2018001764 | 1/2018 |
| WO | WO2018067637 | 4/2018 |
| WO | WO2018073793 | 4/2018 |
| WO | WO2018106424 | 6/2018 |
| WO | 2018/138675 | 8/2018 |

(56) References Cited

FOREIGN PATENT DOCUMENTS

WO  WO2019005039    1/2019
WO  2019/163609     8/2019

OTHER PUBLICATIONS

Written Opinion and International Search Report in International Application No. PCT/IB2020/054641 dated Jul. 15, 2020.
International Search Report and Written Opinion for PCT/AU2021/051281 dated Feb. 15, 2022.
Written Opinion in International Application No. PCT/IB2020/054641 dated May 3, 2021.
European search report issued in EP App. No. 2086392.5 dated Jun. 15, 2022.
Respironics Philips: "Kurzbedienungsanleitung", May 15, 2016, pp. 1-6.
Written Opinion in International Application No. PCT/AU2021/051281 dated Oct. 4, 2022.

* cited by examiner

TWO-WAY COMMUNICATIONS IN A MEDICAL DEVICE

1 CROSS-REFERENCE TO RELATED APPLICATIONS

This application is a continuation of U.S. application Ser. No. 16/875,728, filed May 15, 2020, which claims priority to U.S. Provisional Application No. 62/848,991, filed May 16, 2019, the entire contents of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use, and more particularly to methods and systems for setting up medical devices and providing tailored coaching and/or personalize therapy for patients using the medical devices.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system.=

CPAP therapy is highly effective to treat certain respiratory disorders, provided patients comply with therapy. If a mask is uncomfortable, wrongly sized, difficult to use, ill suited to a particular patient characteristic (e.g. a nasal mask for a mouth breather), or difficult to clean (e.g., difficult to assemble or disassemble) a patient may not comply with therapy.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a respiratory pressure therapy system configured to present a patient with demographic and/or subjective questions and receive answers to the questions so that the questions can be analysed to determine settings for the respiratory pressure therapy system.

Another aspect of one form of the present technology is to, e.g., via advanced analytics, determine tailored coaching programs and/or personalized therapy for a patient based on patient's answers to demographic and/or subjective questions and/or data from a plurality of other users.

One form of the present technology comprises applying settings to a respiratory pressure therapy system based on demographic and/or subjective questions answered by a patient.

Another aspect of one form of the present technology is to present demographic and/or subjective questions and receive answers via a web or mobile application.

Another aspect of one form of the present technology is to receive answers for demographic and/or subjective questions via a web or mobile application and using the answers to determine settings for the respiratory pressure therapy system.

Another aspect of one form of the present technology is a processing system including memory storing a plurality of demographic questions and/or a plurality of objective questions and a computing system configured to: transmit demographic and/or objective questions to a medical device and/or a mobile device configured to execute an application for communicating with the medical device, receiving answers to the questions from the medical device and/or the mobile device, determine, e.g., via advanced analytics, based on the received answers, a tailored coaching program for the patient and/or personalised therapy using the medical device An aspect of certain forms of the present technology is a medical device that is easy to use, e.g. by a person who does not have medical training, by a person who has limited dexterity, vision or by a person with limited experience in using this type of medical device.

Another aspect of the present technology is directed to a respiratory pressure therapy (RPT) system for providing continuous positive air pressure (CPAP) to a patient. The system comprising: a flow generator configured to generate a supply of breathable gas for delivery to the patient, wherein the breathable gas is output from the flow generator at a pressure level that is above atmospheric pressure; at least one sensor that is configured to measure a physical quantity while the breathable gas is supplied to the patient; a computing device including memory and at least one hardware processor. The computing device may be configured to: receive, from the at least one sensor, sensor data that is based on measured physical property of the supply of breathable gas; control, based on the received sensor data, the flow generator to adjust a property of the supply of breathable gas that is delivered to the patient; display, on a display device, one or more questions relating to demographic and/or subjective feedback; responsive to displaying the one or more questions, receive one or more inputs indicating answers to the one or more questions; transmit the answers to a remote processing system; receive, from the remote processing system, settings for the respiratory pressure therapy system determined based on the transmitted answers; and adjust, based on the received settings, control settings of the respiratory pressure therapy system.

In examples, (a) the remote processing system may be an on-demand cloud computing platform configured to perform machine learning using data received from a plurality of patients, (b) the questions may be pre-stored in the memory, (c) the computing device may be further configured to perform setup operations, and the one or more questions may be displayed after the setup and after a predetermined condition is satisfied, (d) the predetermined condition may include a predetermined amount of time passing after setup, (e) the questions may include at least one question relating to demographic information about the patient and at least one question relating to subjective feedback from the patient about using the respiratory pressure therapy system, (f) the system may further include the remote processing system and the remote processing system may be configured to determine tailored coaching programs for the patient based on the answers transmitted to the remote processing system, (g) the system may further include the remote processing system and the remote processing system may be configured to determine personalized therapy for the patient based on the answers transmitted to the remote processing system, (h) the one or more questions may be received from the remote processing system, (i) the system may further include a patient interface configured to engage with at least one airway of the patient and supply breathable gas to the patient, and/or (j) the settings for the respiratory pressure therapy system and/or tailored coaching programs are received by an application, website, email, and/or mobile device associated with the patient.

Another aspect of the present technology is directed to an apparatus for treating a respiratory disorder in a patient. The apparatus comprising: a display device; a pressure generator configured to generate a flow of air for treating the respiratory disorder; a transducer configured to generate a flow signal representing a property of the flow of air; a controller, coupled to the display, the pressure generator, and the transducer. The controller may be configured to: receive the flow signal from the transducer; based on the received flow signal, control the pressure generator to adjust a property of the flow of air; display, to the display device, a request for demographic and/or subjective feedback; responsive to the request, receive one or more inputs representing demographic and/or subjective feedback; transmit demographic and/or subjective feedback data determined based on the received one or more inputs to a remote processing system; receive, from the remote processing system, analysis results determined based on the transmitted demographic and/or subjective feedback data; and adjust, based on the received analysis results, control settings of the apparatus.

In examples, (a) the controller, the display, and the pressure generator may be commonly housed, (b) the adjusted control settings may include a treatment pressure provided in a patient mask coupled to the pressure generator, (c) the analysis results may include tailored coaching programs for the patient, (d) the analysis results may include a personalized therapy for the patient, (e) the controller may be configured to transmit, with the demographic and/or subjective feedback data, operational data of the apparatus, and the analysis results may be determined based on the demographic and/or subjective feedback data and the operational data of the apparatus, (f) the request for demographic and/or subjective feedback may be displayed after a predetermined condition is satisfied, (g) the predetermined condition may be a predetermined time period after the apparatus is set up, and/or (h) the predetermined condition may be a predetermined time period that the apparatus has been operated by the patient.

Another aspect of the present technology is directed to a method of operating a respiratory treatment apparatus for generating a flow of air in order to treat a respiratory disorder. The method comprises: measuring a property of the flow of air, using a transducer; calculating, in a controller and based on the measured property, a result comprising at least one of: a respiratory event, a cardio-respiratory characteristic of a patient, and a physiological state of the patient; controlling, in the controller, an adjustment to a property of the flow of air based on the result; displaying one or more questions relating to demographic and/or subjective feedback; responsive to displaying the one or more questions, receiving, in the controller, one or more inputs indicating answers to the one or more questions; transmitting the answers to a remote processing system; and receiving, from the remote processing system, settings for operating the respiratory treatment apparatus and/or tailored coaching programs for the patient based on the answers transmitted to the remote processing system.

In examples, (a) the method may include adjusting, based on the received settings, control settings of the respiratory treatment apparatus, (b) the settings for operating the respiratory treatment apparatus may provide personalized therapy for the patient determined based on the answers transmitted to the remote processing system and control settings of the respiratory treatment apparatus at a time the inputs indicating answers are received, (c) the questions may be displayed on a display of the respiratory treatment apparatus, (d) the questions may be displayed on a mobile device configured to execute an application for controlling the respiratory treatment apparatus, (e) the questions may be displayed after a predetermined condition is satisfied, (f) the predetermined condition may be a predetermined time period after the respiratory treatment apparatus is set up, and/or (g) the predetermined condition may be a predetermined time period that the respiratory treatment apparatus has been operated by the patient.

Another aspect of the present technology is directed to a processing system comprising: memory storing a plurality of demographic questions and a plurality of objective questions; a computing system including at least one hardware processor coupled to the memory, the computing system configured to: transmit, to a medical device associated with a patient, at least one demographic question and at least one objective question stored in the memory; receive, from the medical device, answers to the at least one demographic question and at least one objective question transmitted to the medical device; transmit, to a mobile device configured to execute an application for communicating with the medical device, a notification indicating that unanswered questions are available; receive, from the mobile device, request for the questions; responsive to the request, transmit, to the mobile device, at least one demographic question and at least one objective question stored in the memory; receive, from the mobile device, answers to the at least one demographic question and at least one objective question transmitted to the mobile device; and perform advanced analytics to determine, based on (1) the answers received from the medical device and the mobile device and (2) answers received from a plurality of other medical devices, a tailored coaching program for the patient and personalised therapy using the medical device.

In examples, (a) the computing system may be further configured to receive, from the medical device, answers to questions pre-stored on the medical device and answered using the medical device, (b) the medical device may be a respiratory treatment apparatus, (c) the questions may be transmitted to the mobile device and/or the medical device after a predetermined condition is satisfied, (d) the predetermined condition may be a predetermined time period after the medical device is setup, and/or (e) the predetermined condition may be a predetermined time period that the medical device has been operated by the patient. The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1 shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 2 shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 3 shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 RPT Device

FIG. 4A shows an RPT device in accordance with one form of the present technology.

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.3 Humidifier

Figure 5A:
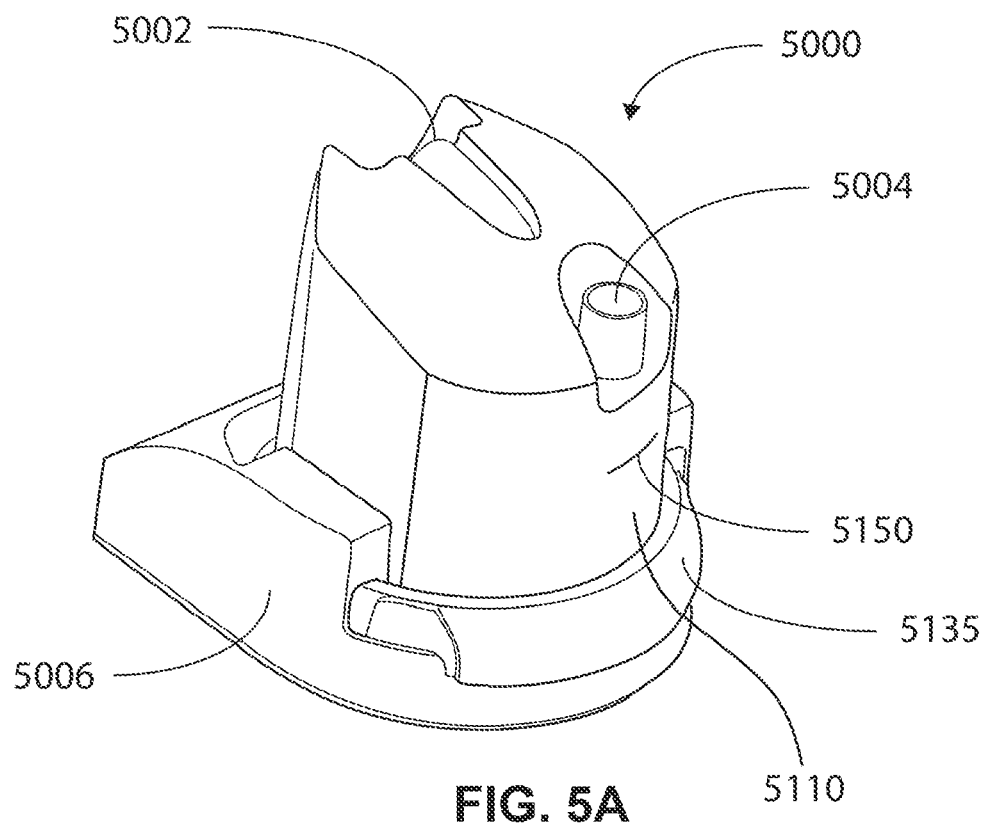

FIG. 5A shows an isometric view of a humidifier in accordance with one form of the present technology.

Figure 5B:
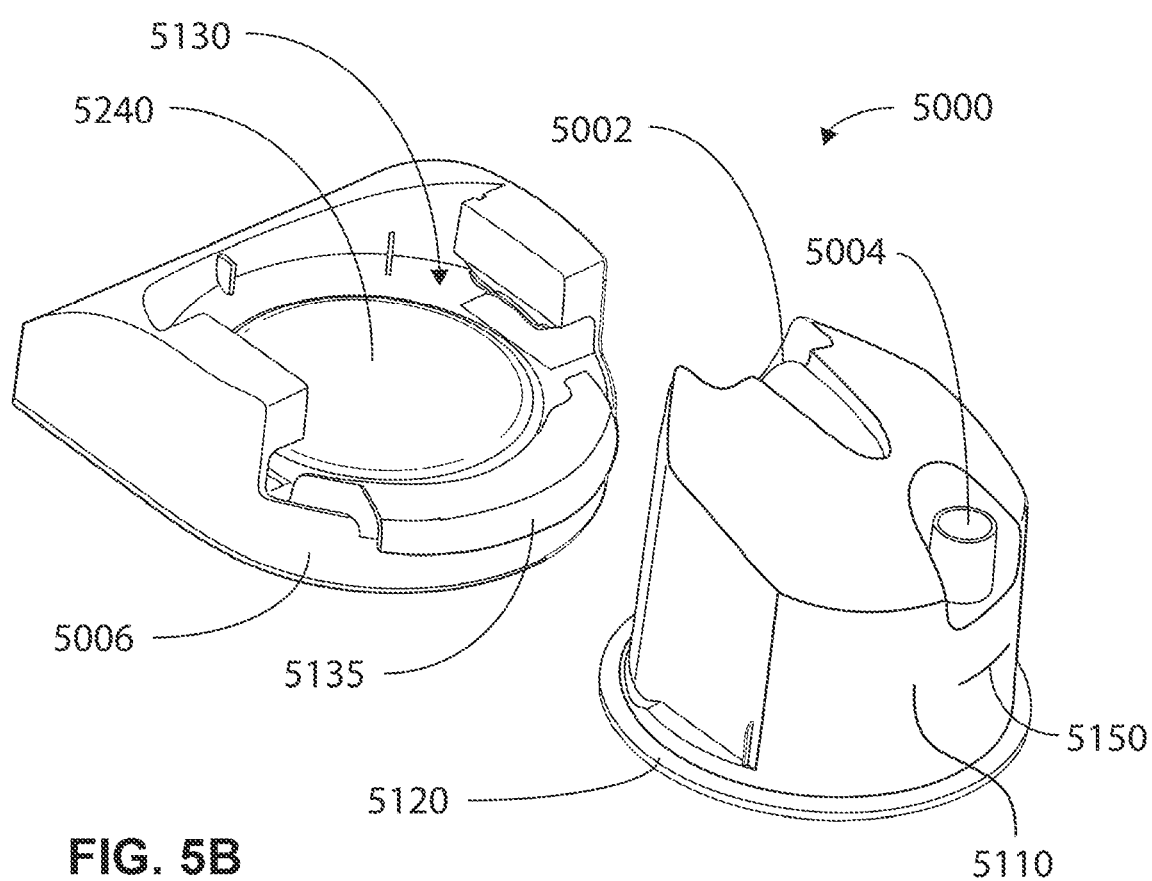

FIG. 5B shows an isometric view of a humidifier in accordance with one form of the present technology, showing a humidifier reservoir 5110 removed from the humidifier reservoir dock 5130.

Figure 5C:
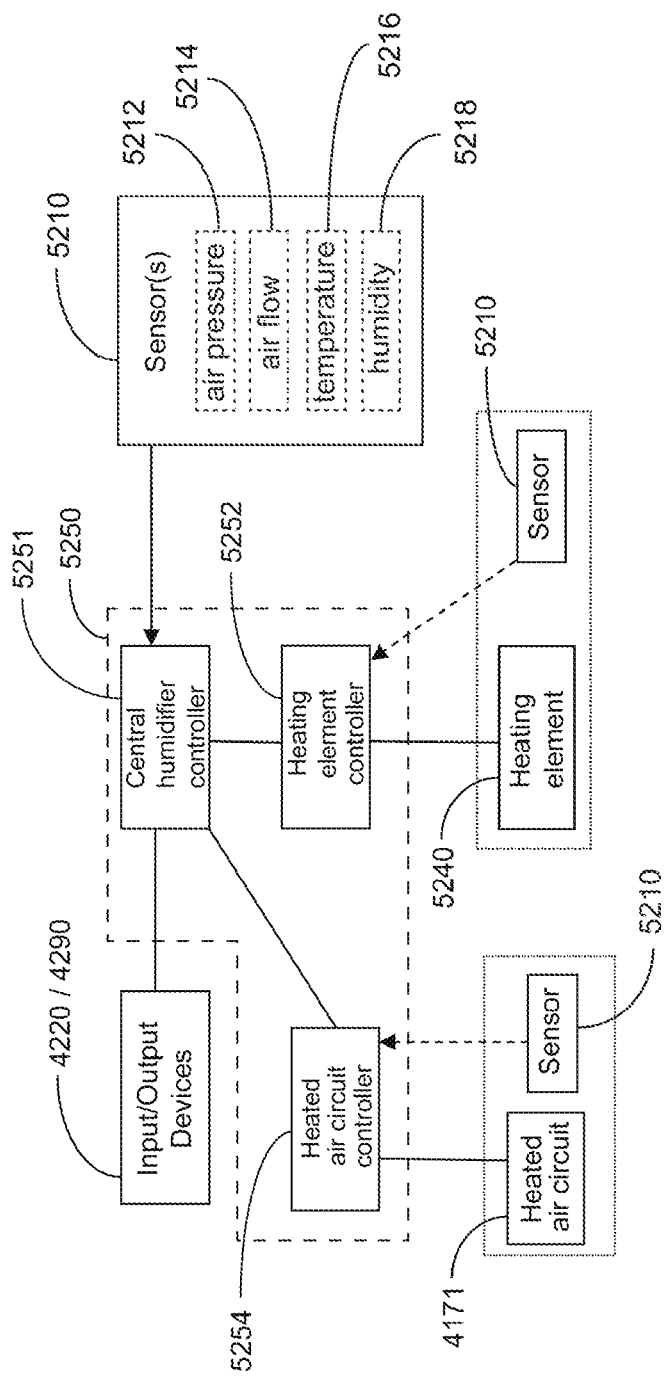

FIG. 5C shows a schematic of a humidifier in accordance with one form of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises one or more of the following functional aspects: a seal-forming structure, a plenum chamber, a positioning and stabilising structure, a vent, one form of connection port for connection to air circuit 4170, and a forehead support. In some forms a functional aspect may be provided by one or more physical components. In some forms, one physical component may provide one or more functional aspects. In use the seal-forming structure is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 4 $cmH_2O$ with respect to ambient, at least 6 $cmH_2O$ with respect to ambient, at least 10 $cmH_2O$ with respect to ambient, at least 20 $cmH_2O$ with respect to ambient, at least 30 cmH$_2$O with respect to ambient or any positive pressure between 4 cmH$_2$O and 30 cmH$_2$O with respect to ambient.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142 including a motor 4144), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

An RPT device may comprise one or more of the following components in an integral unit. In an alternative form, one or more of the following components may be located as respective separate units. For example, the RPT device may comprise one or more of an air filter 4110, side panel, muffler (e.g., muffler 4120, inlet muffler 4122, outlet muffler 4124), pressure generator, pneumatic block, chassis, transducer 4270 (flow transducer, pressure transducer, motor speed transducer), light sensor, anti-spillback valve 4160, air circuit, air circuit connector, oxygen delivery port, power supply, central controller, therapy device controller, protection circuit, data connection interface, memory, output devices (e.g. display, alarms, etc. . . . ) and a user interface panel(s), such as those described in PCT application PCT/AU2014/050426 (WO2015089582), which is incorporated herein by reference.

According to one example, the user interface panel includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.1.1 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.1.2 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.1.2.1 Display Driver

A display driver 4292 receives as an input the characters, symbols, or images intended for display on the display 4294, and converts them to commands that cause the display 4294 to display those characters, symbols, or images.

5.4.1.2.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.2 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules. The modules may include a pre-processing module 4310 providing pressure compensation 4312, vent flow rate estimation 4314, leak flow rate estimation 4316, and respiratory flow rate estimation 4318. The processing of the pre-processing module 4310 may be used as an input into a therapy engine module 4320. The therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329. A therapy control module 4330 receives as inputs the therapy parameters from the therapy parameter determination algorithm 4329 of the therapy engine module 4320, and controls the pressure generator 4140 to deliver a flow of air in accordance with the therapy parameters. In one form of the present technology, the central controller 4230 executes one or more methods 4340 for the detection of fault conditions. Details regarding one or more operations performed by algorithms are described in the PCT application PCT/AU2014/050426 (WO2015089582), which is incorporated herein by reference.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.6 Two-Way Communication for Personalised Therapy and/or Coaching

In one form of the present technology, a medical device (e.g., a RPT device) may include two-way communication with one or more remote processing system to facilitate tailored coaching programs, personalized therapy, and/or targeted care. The medical device may be configured to capture data and/or transmit the data to the remote processing system for processing. The captured data may include, sensor data, demographic feedback, and/or subjective feedback. The remote processing system may perform patient segmentation and/or advanced analytics using the received data and provide the medical device with tailored solutions. The tailored solutions may include tailored coaching programs for increased engagement and motivation, personalized therapy with automated comfort and/or therapy setting updates to increase long term adherence, and/or targeted care and follow up based on knowing which patients need help. The patient segmentation and advanced analytics may include performing machine deep learning using data from other users and using one or more trained models to provide the tailored solutions.

Unlike conventional systems in which settings for a medical device had to be pre-loaded and were modified by a highly trained technician, examples of the present technology provide for the medical device to be configured automatically after the device is deployed for use. The settings for the medical device and recommendations for the patient can be accurately determined remotely and quickly without needing a clinician to perform multiple iterations of modifying the device settings before a patient feels comfortable when using the medical device. In addition, the feedback received from the user and settings of the medical device can be used to improve settings of other medical devices and provide relevant recommendations to other patients.

Figure 1:
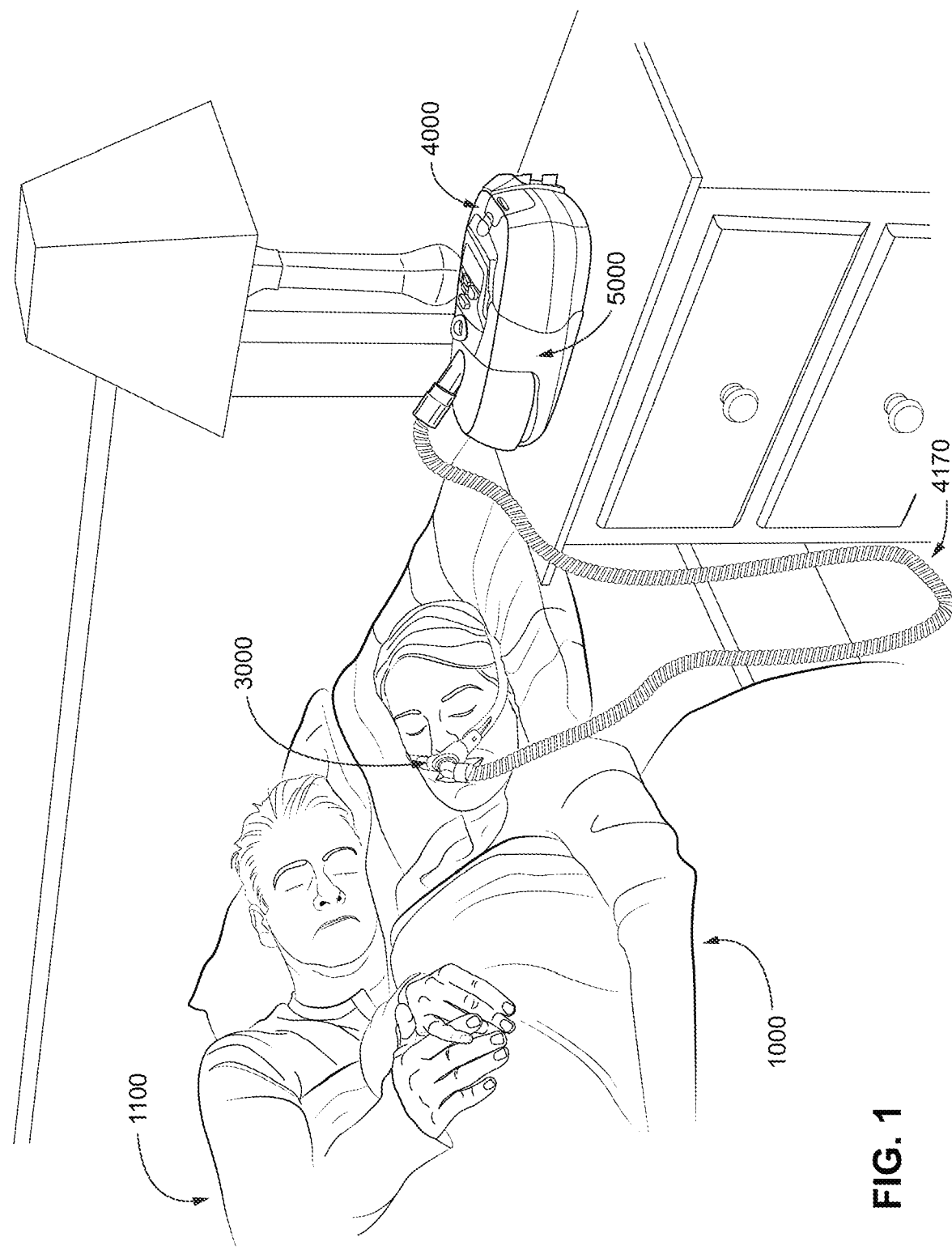
Figure 2:
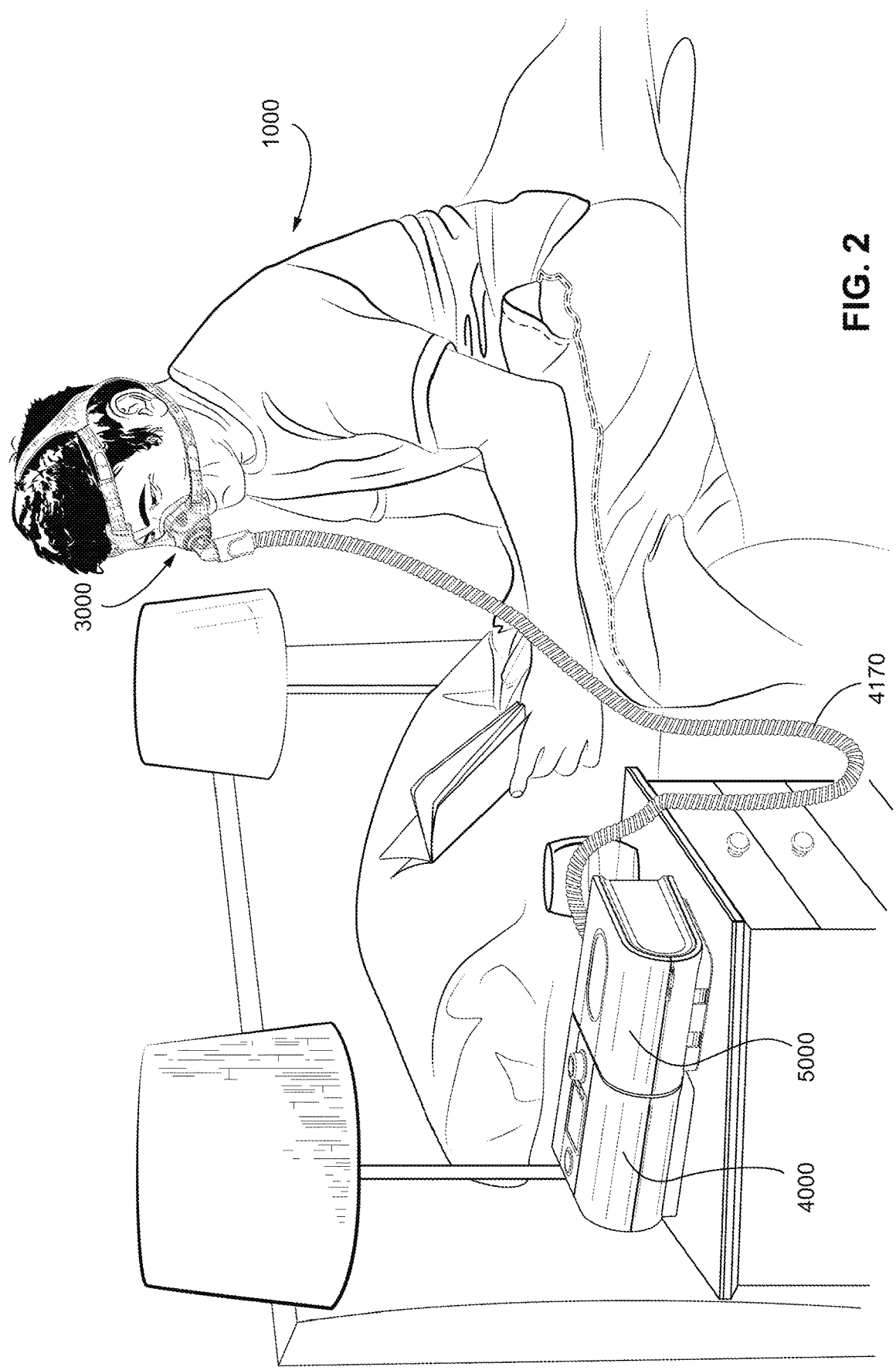
Figure 3:
Figure 4A:
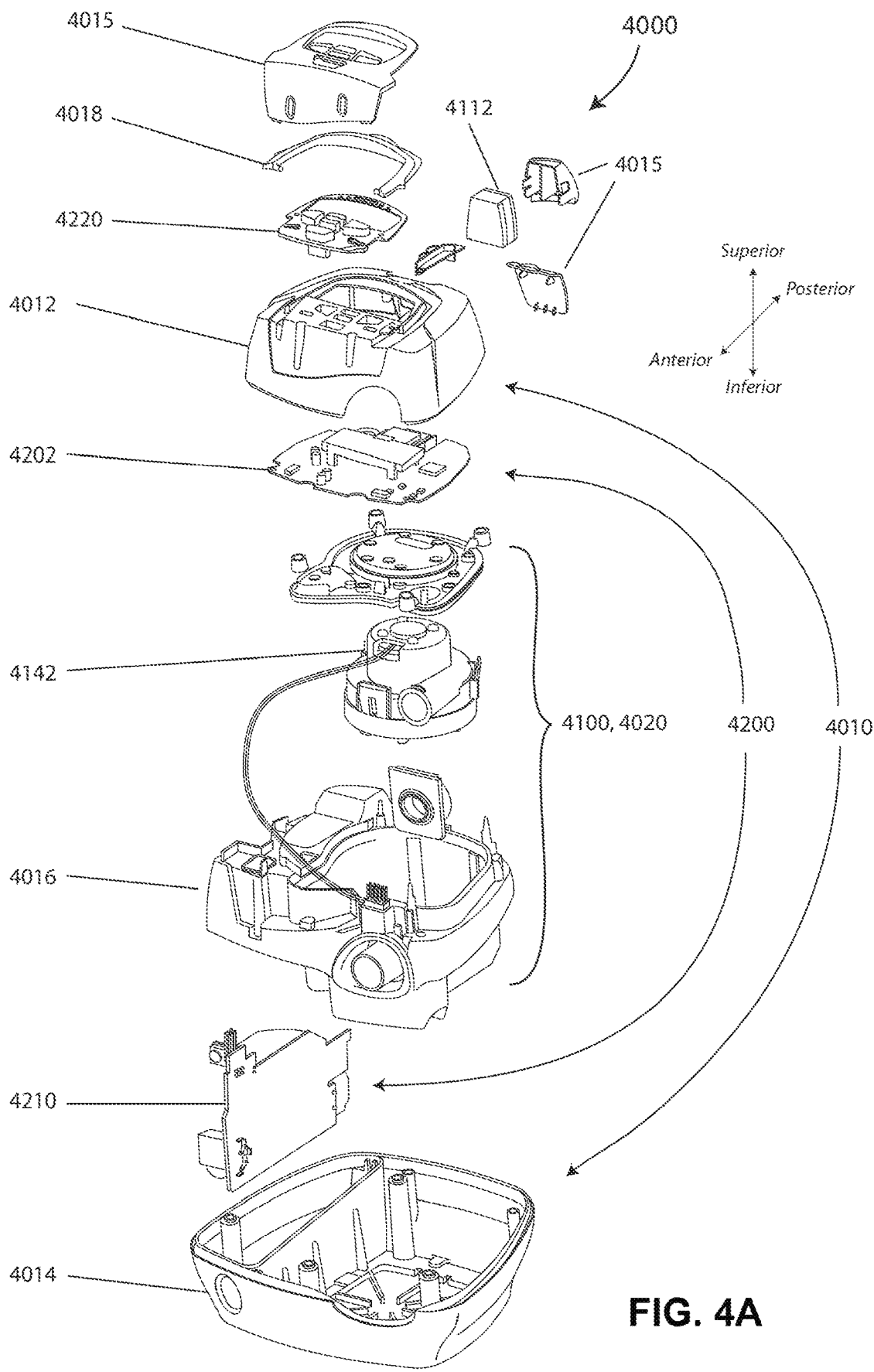
FIG. 4C is a schematic diagram of the electrical components of an RPT device in accordance with one form of the present technology.
FIG. 4D is a schematic diagram of the electrical components of an RPT device in accordance with one form of the present technology.
FIG. 4E is a schematic diagram of the algorithms implemented in an RPT device in accordance with one form of the present technology.
FIG. 4F is a flow chart illustrating a method carried out by the therapy engine module of FIG. 4E in accordance with one form of the present technology.
FIG. 4G shows a diagram of a communication system between an RPT device and a remote computing system in accordance with one form of the present technology.
FIG. 4H shows exemplary operations performed by an RPT device and a remote computing system in accordance with one form of the present technology.
FIG. 4I shows example display screens including demographic and/or subjective feedback requests that may be displayed to a patient in accordance with one form of the present technology.
FIG. 4J shows another example of operations performed by an RPT device and a remote computing system in accordance with one form of the present technology.
FIG. 4K shows a data flow diagram in a system providing communication between a medical device, a patient portal 8030 and a patient survey service 8010 in accordance with one form of the present technology.
Figure 4B:
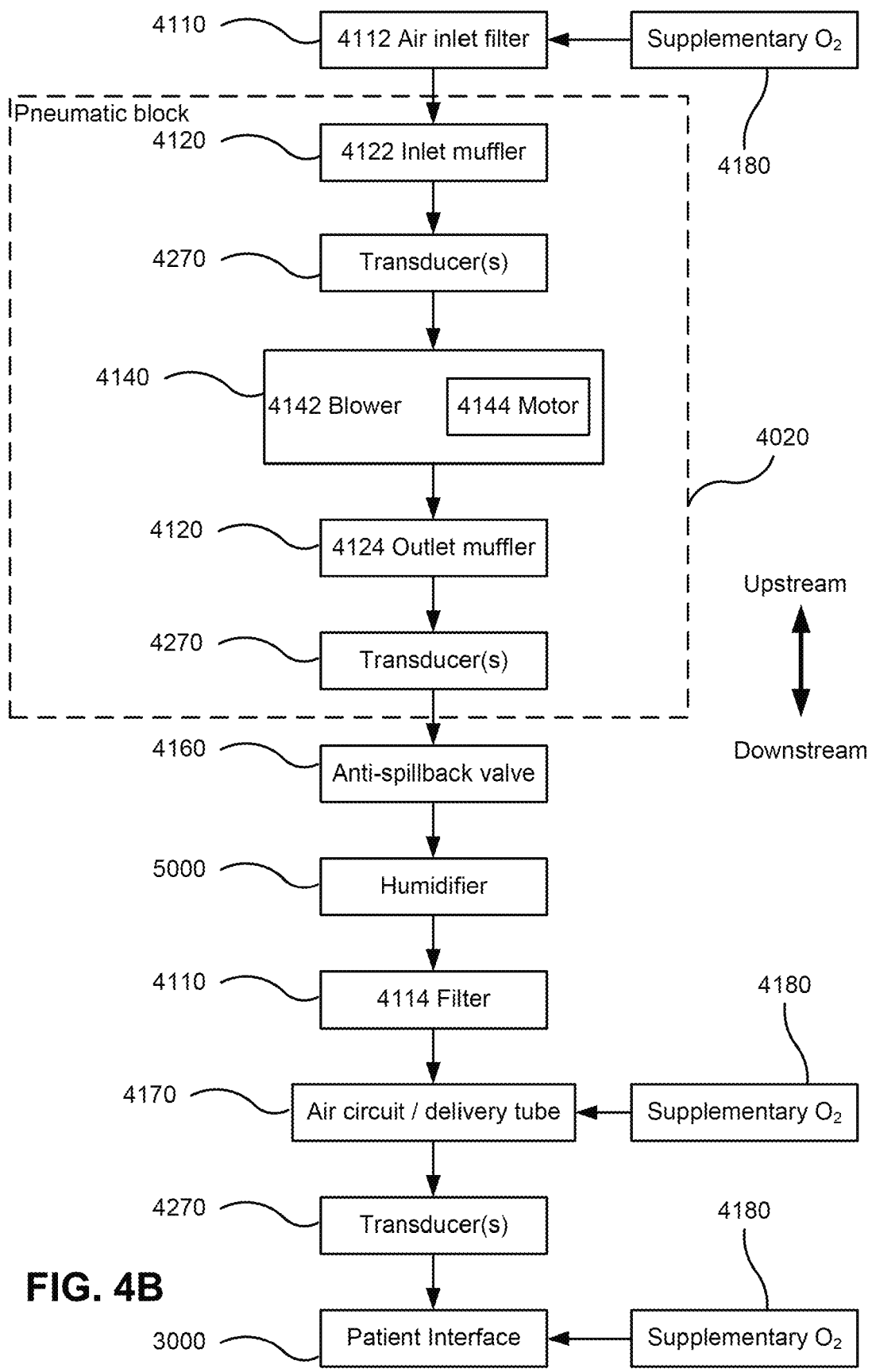
Figure 4C:
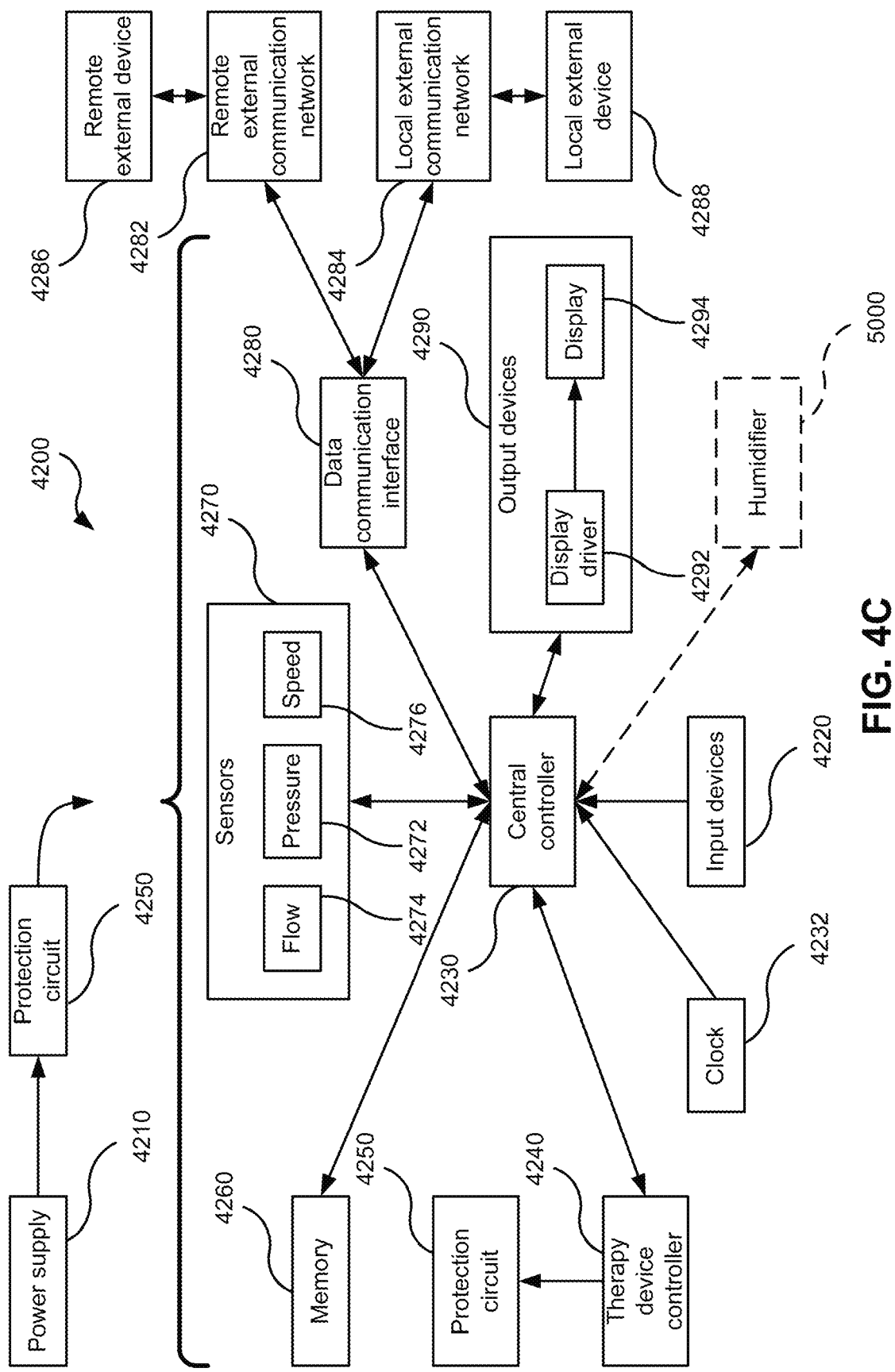
Figure 4D:
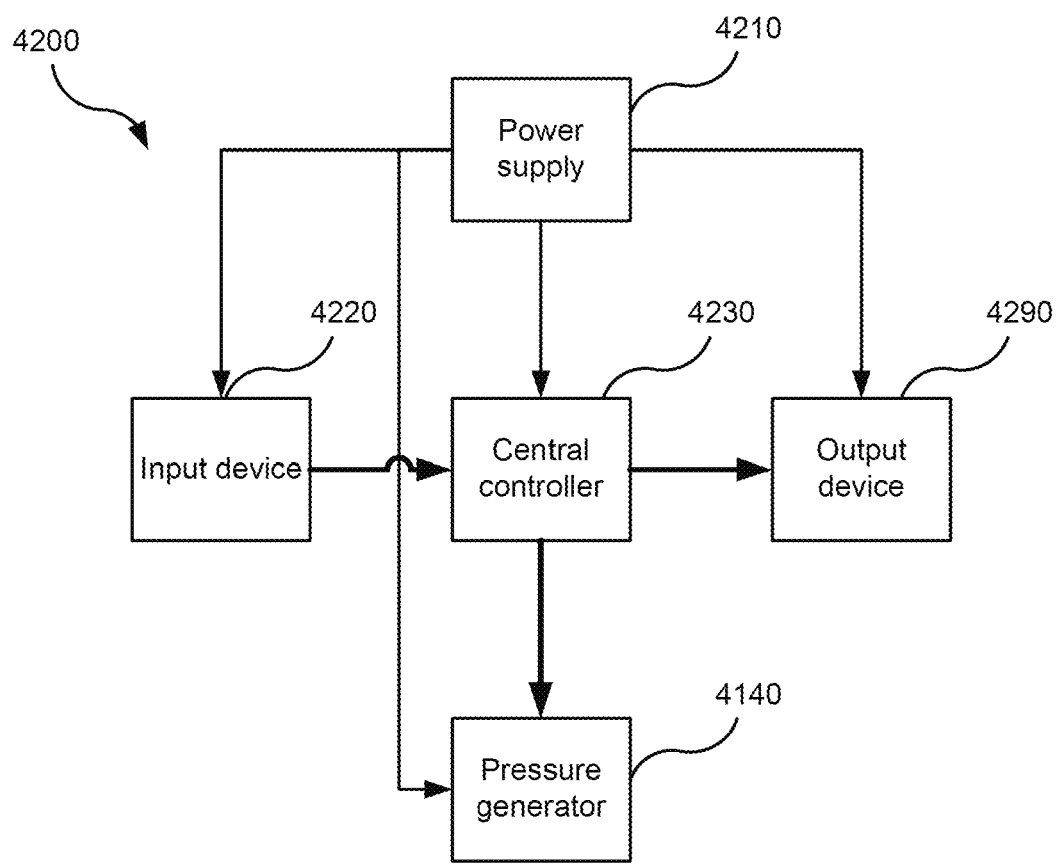
Figure 4E:
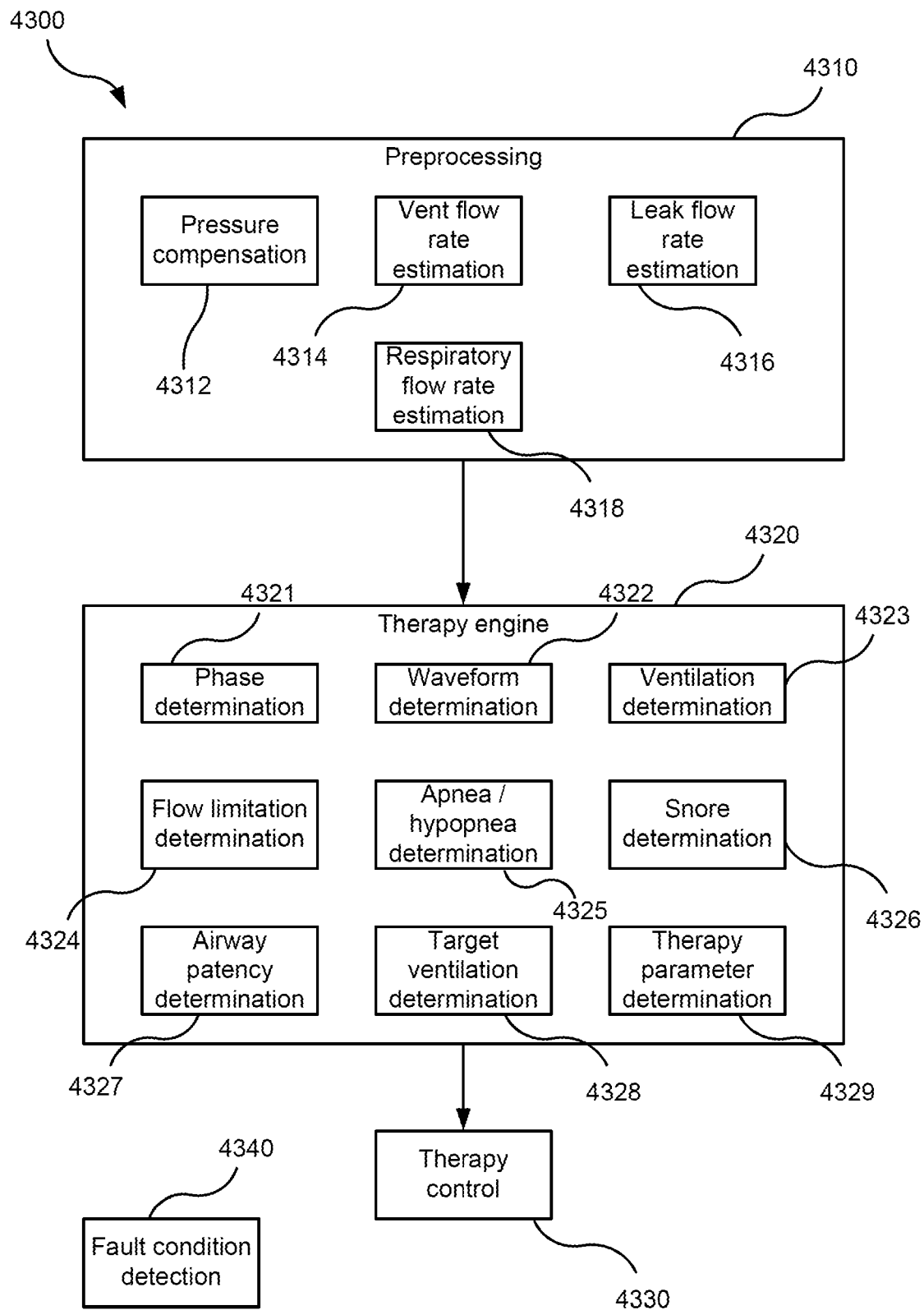
Figure 4F:
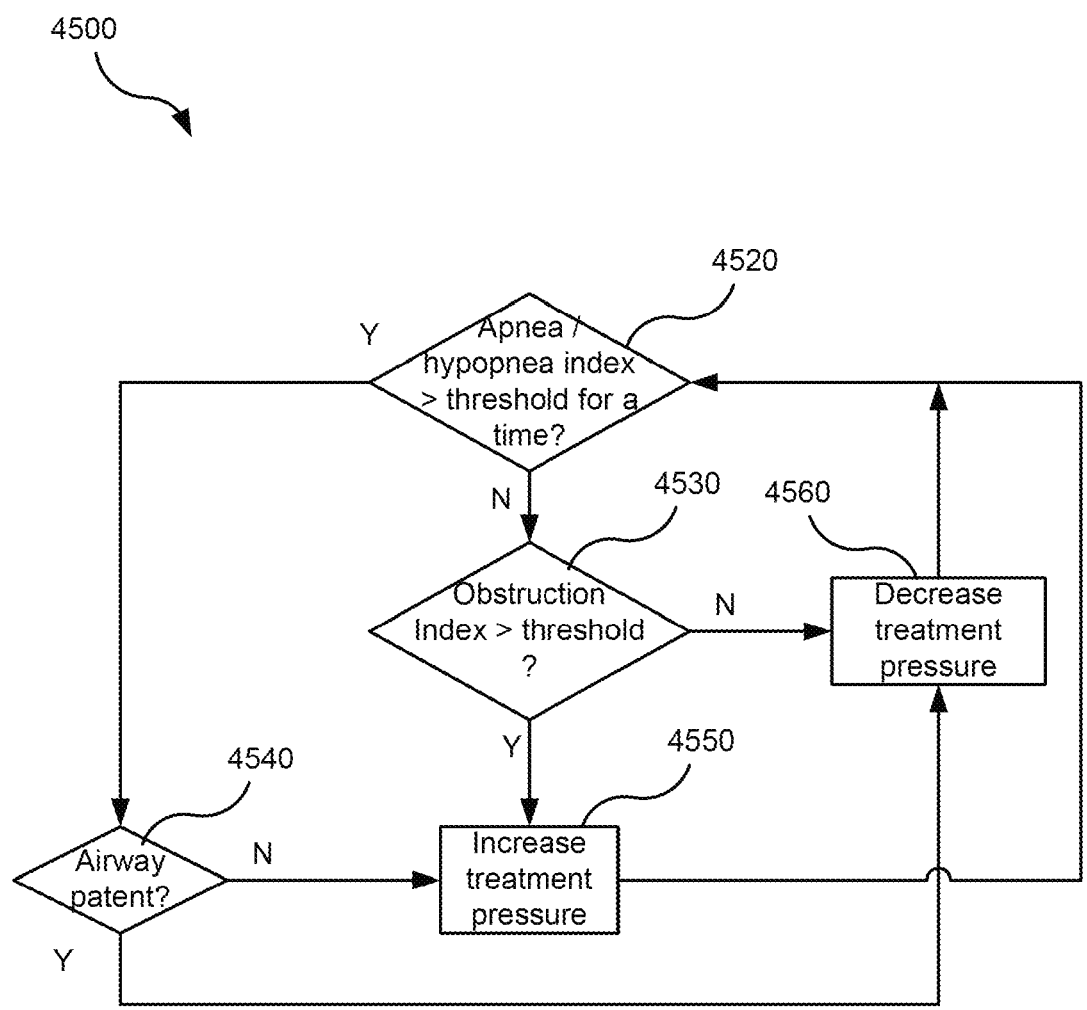
Figure 4G:
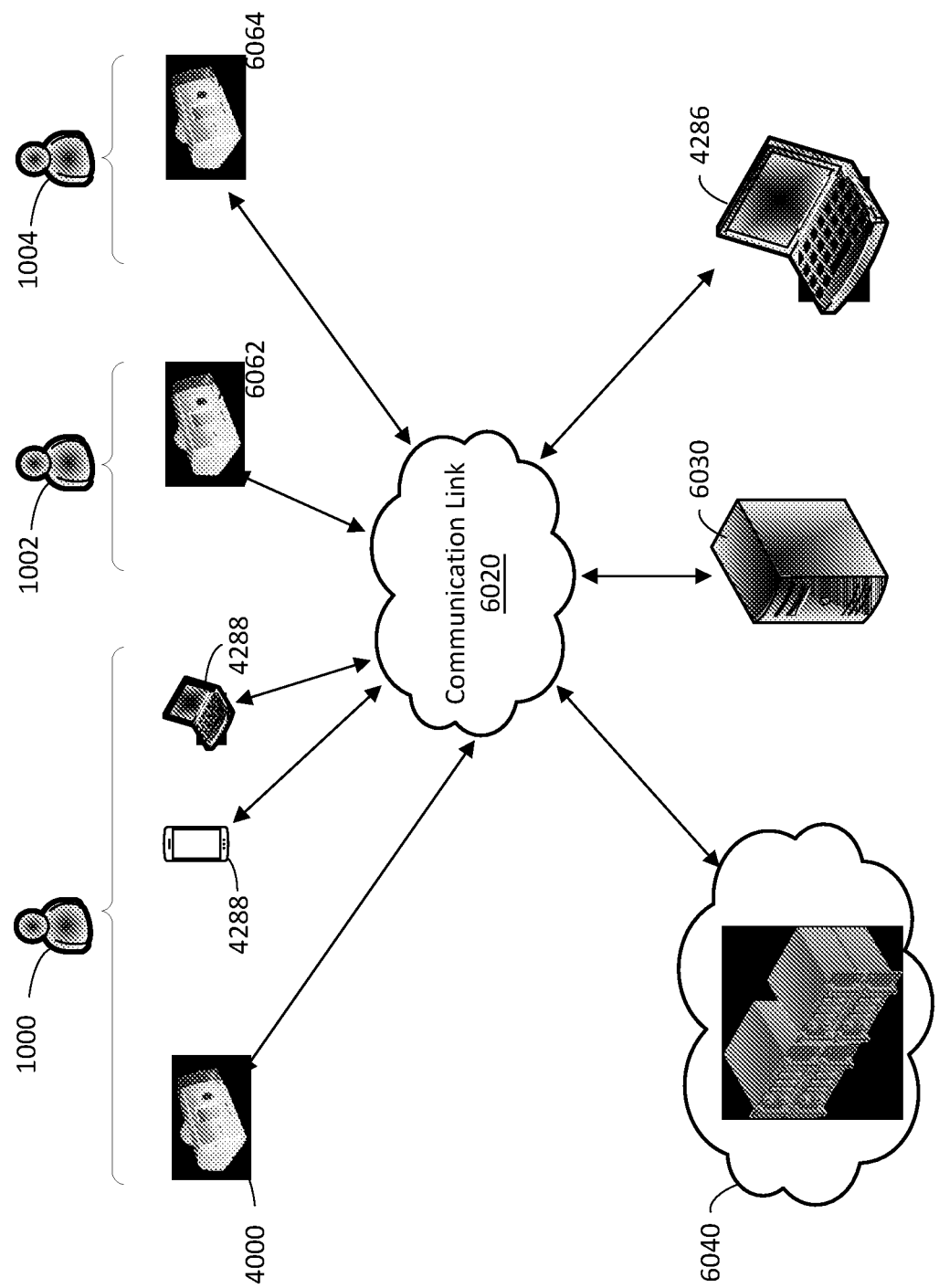

FIG. 4G shows a diagram of a communication system between an RPT device 4000 and a remote computing system. FIG. 4G includes one or more RPT devices 4000 associated with a patient 1000. The present technology is not limited to RPT device, but may be applied to other medical devices. The RPT device 4000 may be configured to communicate via a data communication interface 4280 with a remote external device 4286 and/or local external devices 4288 (e.g., a personal computer, mobile phone, tablet and/or remote control) and/or remote external device. The local external devices 4288 may be configured to communicate directly with the RPT device 4000 when located in the vicinity of the RPT device 4000 or remotely via a local or external network when the local external device 4288 is not located near the RPT device 4000. The remote external device 4286 may be accessible to an appropriately authorised person such as a clinician, manufacturer, and/or supplier of the device. As shown in FIG. 4G, the RPT device 4000 may also communicate with a remote computing system including a server 6030 and/or a cloud computing platform 6040 (e.g., Amazon Web Services™, Google™ cloud platform, Microsoft™ Azure).

One or more other medical devices 6062 or 6064 (which may be RPT devices), associated with other patients 1002 and 1004, may be configured to communicate with the remote external device 4286, the server 6030 and/or the cloud computing platform 6040.

The devices illustrated in FIG. 4G may communicate via a communication link 6020 comprising a remote external communication network 4282 and/or a local external communication network 4284.

The RPT device 4000 and/or medical devices 6062 and 6064 may be configured to transmit, via the communication link 6020, sensor data, demographic feedback, and/or subjective feedback to the server 6030 and/or the cloud computing platform 6040. The server 6030 and/or the cloud computing platform 6040 may be configured to perform patient segmentation and/or advanced analytics using the received data and provide the RPT devices with tailored solutions. The tailored solutions may include tailored coaching programs, personalized therapy, and/or targeted care.

Figure 4H:
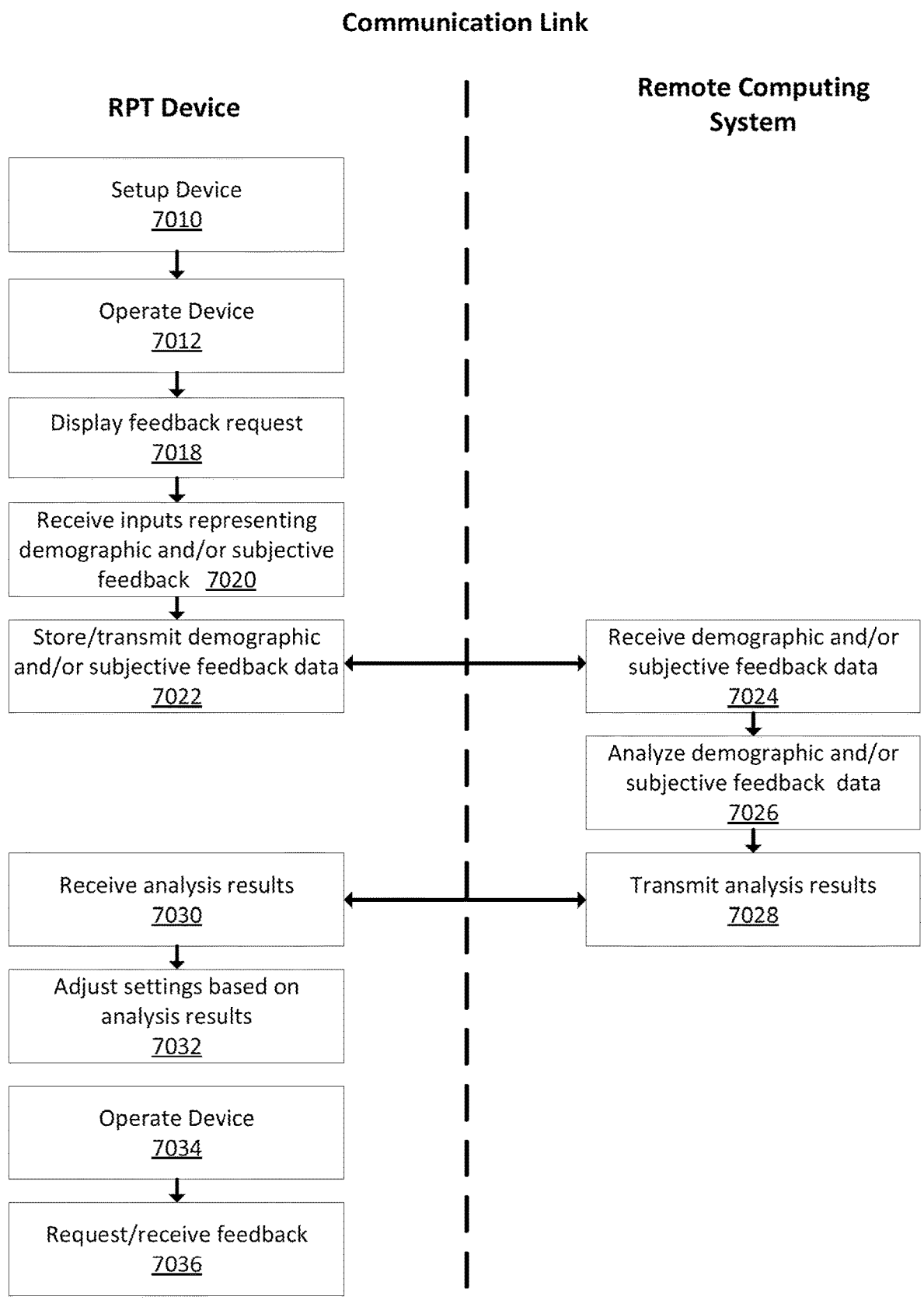
Figure 41:
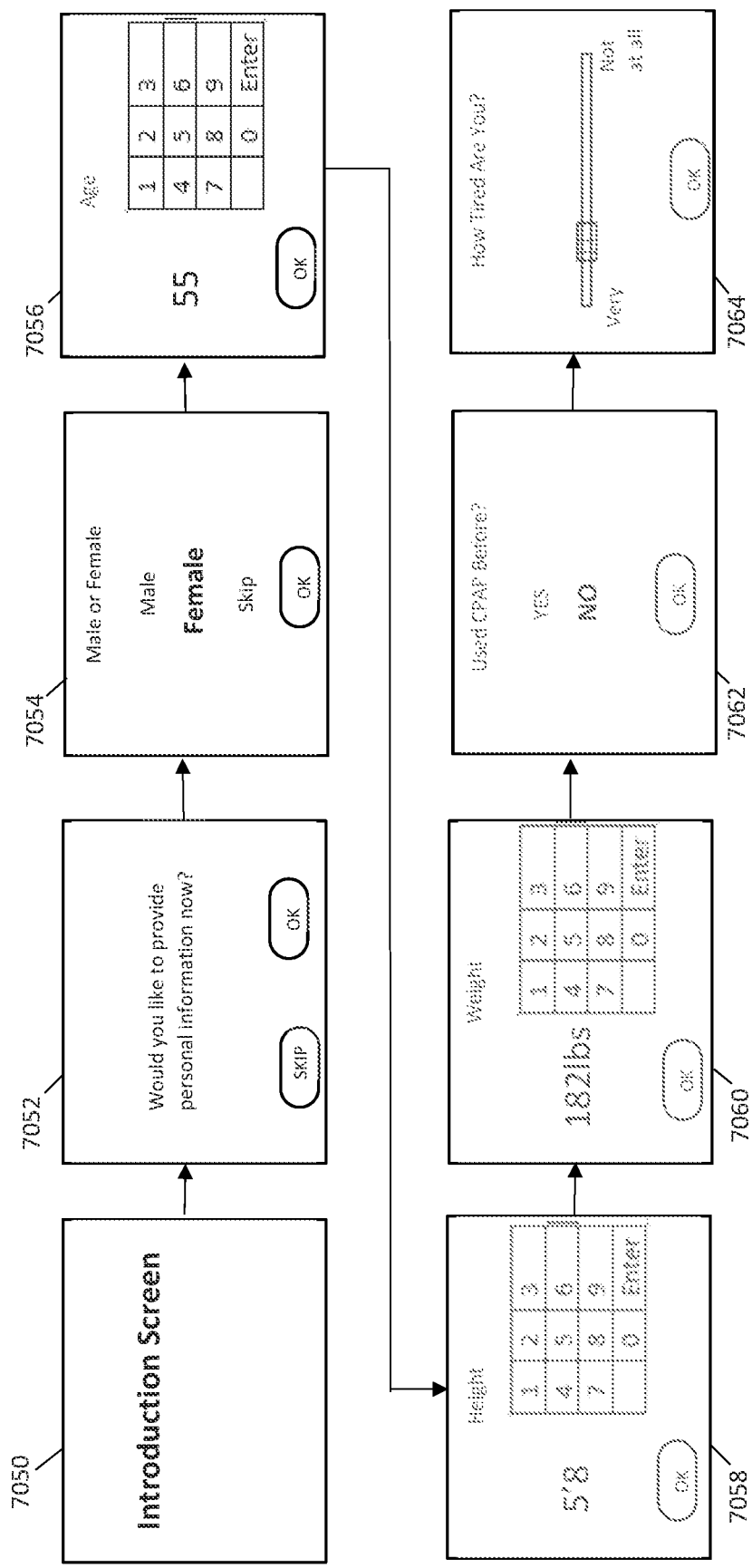

FIG. 4H shows exemplary operations performed by an RPT device 4000 and a remote computing system in accordance with one form of the present technology. While FIG. 4 shows the operations being performed by specific devices, the operations shown are not so limited. One or more operations may be performed by other devices operationally coupled to the RPT device 4000 and/or remote computing system. In some examples, one or more operations shown as being performed by the RPT device 4000 may be performed using a web or mobile application executing on another device (e.g., a local external device 4288).

The RPT device 4000 may be configured to perform setup of the RPT device 4000 (step 7010). The setup may include associating a patient with the RPT device 4000, configuring initial settings of the RPT device 4000 for the patient, and/or providing instructions on how to use the device. One or more operations disclosed in U.S. Provisional Application No. 62/749,430 filed on Oct. 23, 2018, titled "SYSTEMS AND METHODS FOR SETUP OF CPAP SYSTEMS", and U.S. application Ser. No. 16/661,250 filed on Oct. 23, 2019, titled "SYSTEMS AND METHODS FOR SETUP OF CPAP SYSTEMS", each of which is hereby incorporated by reference in its entirety, may be performed during setup of the RPT device 4000.

The setup may be performed when the RPT device 4000 is powered on for a first time after being purchased or reset, or when the RPT device 4000 is assigned to a new patient. The setup may be performed without user interaction by applying settings for the RPT device 4000 stored in memory (e.g., memory 4260 or memory external to the RPT device 4000) or receiving instructions from a remote external device 5286 controlled by a clinician, manufacturer, and/or distributer of the device.

Patient inputs may be requested and received during the setup from the RPT device 4000 and/or other devices. In some examples, instructions and/or questions may be provided using the output devices 4290 and the patient inputs may be received by using the input devices 4220. In other examples, only the RPT device 4000 may be used to receive the inputs during the setup. In other examples, a local external device 4288 may be used, instead of or in addition to the RPT device 4000, to receive user inputs for setting up the RPT device 4000. Display screens may be generated on the RPT device 4000 and/or the external device to request patient inputs during the setup of the device. In some examples, audio instructions and/or audible responses may be received by the RPT device 4000 and/or local external device 4288. In some examples, the data input by a user and/or tailored coaching programs, personalized therapy, and/or targeted care and follow up (e.g., provided in response to the input data) may be provided via a range of different mechanisms (e.g., applications, web, email, phone etc.).

The RPT device 4000 may be operated (step 7012) based on the setting of the device made during the setup. During operation of the RPT device 4000, the operation of the device may be adjusted based on sensor data (e.g., flow sensor 4274, pressure sensor 4272, and/or speed sensor 4276) and/or additional settings received from the patient and/or clinician.

After one or more predetermined conditions are satisfied, feedback requests may be displayed to the patient (step 7018). The feedback request may be displayed on the display 4294 or the device and/or the local external device 4288 (e.g., in an application). The feedback request may request demographic and subjective feedback from the user in the form of a question or instruction. The feedback request may be made automatically when the predetermined condition is satisfied. The feedback is not limited to demographic and subjective feedback and may include additional questions. The feedback, demographic, and/or subjective feedback may include sleep study result, symptoms, comorbidities or other health information, including the presence of other sleep issues (e.g., insomnia), level of knowledge on sleep apnea, level of comfort in approaching therapy, stage in the pathway (new to therapy or experienced user), and/or motivation.

The predetermined condition may include a predetermined amount of time passing after the RPT device 4000 is setup, the patient reaching a specified goal such as using the device for a predetermined period of time (e.g., a pre-set number of hours, days, or weeks), using a specific feature offered by the RPT device 4000 (e.g., operating the device in a low power mode) a predetermined number of times or for a predetermined time period, completing setup of the RPT device 4000, receiving a signal from the remote computing system or device operated by a clinician, receiving feedback requests from another device, having a flag set indicating that feedback requests are available for display to the patient, and/or receiving a notification that feedback request are available for download.

Responsive to the feedback request, inputs may be received representing the patient's demographic and/or subjective feedback (step 7020). The inputs may be received using only the RPT device 4000 (e.g., via the input devices 4220), only the local external device 4288, or the RPT device 4000 and the local external device 4288.

FIG. 4I shows example display screens including demographic and/or subjective feedback requests that may be displayed to a patient. The feedback requests may be displayed on a display 4294 of the RPT device 4000 and/or display associated with the local external device 4288. While FIG. 4I shows the display screens in a specific order, implementation is not so limited. One or more of the display screens may be provided in a different order or not included in the sequence. One or more other display screens may also be included in the sequence.

Introduction screens 7050 and 7052 may include an introduction text, graphics, and/or a video with information introducing the patient to the personalisation features of the system, components, and/or therapy. Introduction screen 7050 may be displayed for a predetermined period of time before automatically transitioning to display screen 7052. Display screen 7052 may provide selectable options for the user to continue with responding to the displayed feedback request or skipping the personalisation feature of the RPT device 4000. In some examples, instead or in addition to skipping the personalisation feature, the user may be provided with an option to provide the information later. The introduction screens 7050 and/or 7052 may be displayed only when the unit is first turned on by a user (e.g., after purchasing the unit or after resetting) or a predetermined number of times until personalized information is received.

Display screen 7054 shows an option for the patient to select his or her sex. As shown in display screen 7054, the patient may be provided a selectable option to skip the feedback request. One or more of the other feedback requests may also include an option to skip a response request.

Display screen 7056 shows an option to enter a patient's age. In other examples, the feedback request may include entering day, month, and/or year of the patient's birthday.

Display screen 7058 shows an option to enter a patient's height and display screen 7060 shows an option to enter a patient's weight.

Display screen 7062 show a question for whether the patient has used the RPT device 4000 before. In some examples, the question may include providing a number of other RPT devices the patient has used, or level of expertise the patients thinks they have on a predetermined scale in using the RPT device 4000.

Display screen 7064 shows a question for the patient to rate how sleepy they usually feel during the day. The user may be provided with a varying scale between not being sleepy and being very sleepy. Other subjective sleep feedback questions may include sleep regularity, sleep satisfaction, sleep alertness, sleep timing, sleep efficiency, and/or sleep duration. The questions may include: do you usually wake up about the same time (within 1 hour) every day, how often are you satisfied with your sleep, how often are you able to stay awake all day without dozing or napping, is the period of 2 am to 4 am usually in the middle of your night-time sleep, are you usually awake for less than 39 min throughout the night, and/or do you usually sleep between 6 and 8 hours per day. One or more of the responses to the questions may be provided with a sliding scale and/or plurality of selectable responses (e.g., rarely, sometimes and usually).

In one example of the present technology, the feedback may include non-subjective feedback. The feedback may include an apnea-hypopnea index entered by the patient and/or retrieved form a database or a physician or clinician.

Based on the results of the feedback, the patient may be assigned a sleep score, coaching programs and/or personalized therapy of the patient. This information may be determined by the RPT device 4000 and/or other devices (e.g., devices shown in FIG. 4G). The sleep score may be displayed to the patient and/or updated as additional feedback is received periodically from the patient.

Other display screens may include other feedback requests such as, level of how well the patient slept at night, mask comfort level, comfort of breathing while using the CPAP, and/or satisfaction level with operation of the device. In some example, the subjective questions (e.g., comfort of sleep) may be received a plurality number of times, each for a different time period. For example, the RPT device 4000 may be configured to request a patient to provide feedback on the comfort of sleep for a predetermined number of days (e.g., seven days).

The display screens requesting feedback may include an option to select that the response is now known and/or provide with an option to retrieve the information from an external source (e.g., a database, physician's records, external device etc.).

In some examples, a single feedback request may be displayed on the display or two or more feedback requests may be displayed simultaneously on a single screen. For example, the request to enter the age and the height of the patient may be simultaneously displayed on one screen.

In one form of the present technology, the display screens with feedback requests may be displayed on a touch input display. In one form of the present technology, inputs to the questions displayed on the display may be input using one or more input devices 4220 including physical buttons, switches or dials, or software devices accessible via the touch screen.

In one form of the present technology, the feedback requests may be audibly output to the patient using speakers and/or verbal feedback responses may be captured via a microphone.

After the responses to the feedback requests are received, the responses can be stored in memory and/or transmitted (step 7022) to the remote computing system. In one form of the present technology, the data may be transmitted directly to an on-demand cloud computing platform (e.g., Amazon Web Services™, Google™ cloud platform, Microsoft™ Azure). The responses may include demographic and/or subjective feedback data. In one form of the present technology, if a connection to the remote computing system is not available the feedback data may be stored in memory 4260 until the connection becomes available.

In step 7022, other data may be transmitted with the feedback data to the remote computing system. For example, the other data may include therapy data for determining whether the patient has used the RPT device according to the compliance rule, the RPT device 4000 identification information (e.g., serial number), the RPT device 4000 location information, user profile data, data captured by sensors (e.g., transducer 4270), settings applied during setup of the RPT device 4000, type of accessories coupled to the RPT device 4000, and/or modification made to settings by the patient and/or when such modifications were made.

The remote computing system, receives data (step 7024), analyses the data (step 7026), and transmits analysis results (step 7028) to the RPT device 4000 and/or web or mobile application. The remote computing system may receive the demographic and/or subjective feedback, and other data from the RPT device 4000 or local external device. The data may be directly received by the remote computing system for processing. The remote computing system may include a server 6030 and/or a cloud computing platform 6040. The server 6030 may be a non-cloud based server managed by the manufacturer or clinician.

The remote computing system may segment the patient's data (e.g., age range, gender, weights, environment, etc. . . . ), and use models developed using similar and/or different data from other users to determine what the patient needs and/or what settings on the RPT device 4000 should be modified.

The models may be predetermined by advanced analytics, artificial intelligence, and/or machine learning. The remote computing system may include models determined based on information about operation of other RPT devices (e.g., medical devices 6062 and/or 6064) associated with other patients 1002 and/or 1004, and demographic and subjective feedback received from the other patients 1002 and/or 1004. The advanced analytics, artificial intelligence, and/or machine learning may be performed on data from a large number of patients and the models may be updated with new data as new data (e.g., data including demographic feedback, subjective feedback, and/or changes to compliance standards) become available. The analysis results may include tailored coaching programs, personalized therapy, and/or targeted care and follow up.

In response to transmitting the feedback data, the RPT device 4000 may receive analysis results (step 7030) from the remote computing system. The analysis results may include tailored coaching programs, personalized therapy, and/or targeted care and follow up.

The tailored coaching programs may be provided to increase engagement and motivation of the patient. The tailored coaching programs may include instructions on how to properly use the device, explain benefits of using features provided by the device, and/or suggest other medical devices and/or accessories that may be beneficial for the patient. For example, information about an accessory (e.g., different type of mask) that will improve the patient's experience using the RPT device 4000 may be displayed on the display 4294 or the local external device 4288.

The personalized therapy may provide for automated comfort setting which have been proven to increase long term adherence (LTA). The personalized therapy may be automatically applied to the RPT device 4000 without patient interaction. In some examples, the patient may be provided with information about changes to the therapy and be requested to accept the proposed changes before they are applied.

The targeted care and follow up may include notifying the patient of need to make modifications in care or need to schedule a meeting with a clinician or another expert. In some example, the RPT device 4000 and/or the local external device 4288 may be used to schedule and/or conduct a meeting with a clinician or other expert.

The analysis results may be used to adjust settings (step 7032) of the RPT device 4000. Modifying the settings may include adjusting one or more comfort settings of the RPT device 4000. For example, the analysis results may include instructions to modify, pressure ramp settings, expiratory relief settings, humidity settings, and air temperature settings. In one form of the present technology, the analysis results may indicate that continued use of the RPT device 4000 is not safe and the use of the RPT device 4000 may be disabled.

After the analysis results are applied, the operation of the RPT device 4000 may be continued (step 7034). Applying the analysis results and operating the RPT device 4000 using the updated settings will control the RPT device 4000 more effectively to meet the needs of the patient. In some example, the modifications may be made to operate the device more efficiently (e.g., using less power or lower temperature of a heated tube delivering air) without significantly sacrificing the patients comfort.

After a predetermined time, one or more of the feedback requests made earlier and/or new feedback requests may be presented to the patient and responses received (step 7036). The response may be used to determine whether the previously applied settings were effective and/or whether additional changes to the operation and/or use of the RPT device 4000 need to be made. The additional feedback request may be made periodically or when new feedback requests are made available by the remote computing system.

In some examples, the additional feedback request may be displayed every time the user powers on the RPT device 4000. When the RPT device 400 is used, the patient may be displayed with a sleep score, a daily insight (e.g., daily recommendation that may be tailored based on the patients and/or other patient's feedback). Providing the additional feedback may include the user updating one or more of the previously provided feedback (e.g., age, height, weight and/or sleep feedback).

In one form of the present technology, some feedback requests may be presented on the RPT devices 4000 and other feedback requests may be presented on the local external device 4288 or another medical device associated with the same patient 1000. Feedback requests that are presented on one device may be marked as displayed and not requested on other devices.

In one form of the present technology, the operations relating to displaying feedback requests and receiving inputs for the feedback requests may be performed during the setup (step 7010) of the device.

Figure 4J:
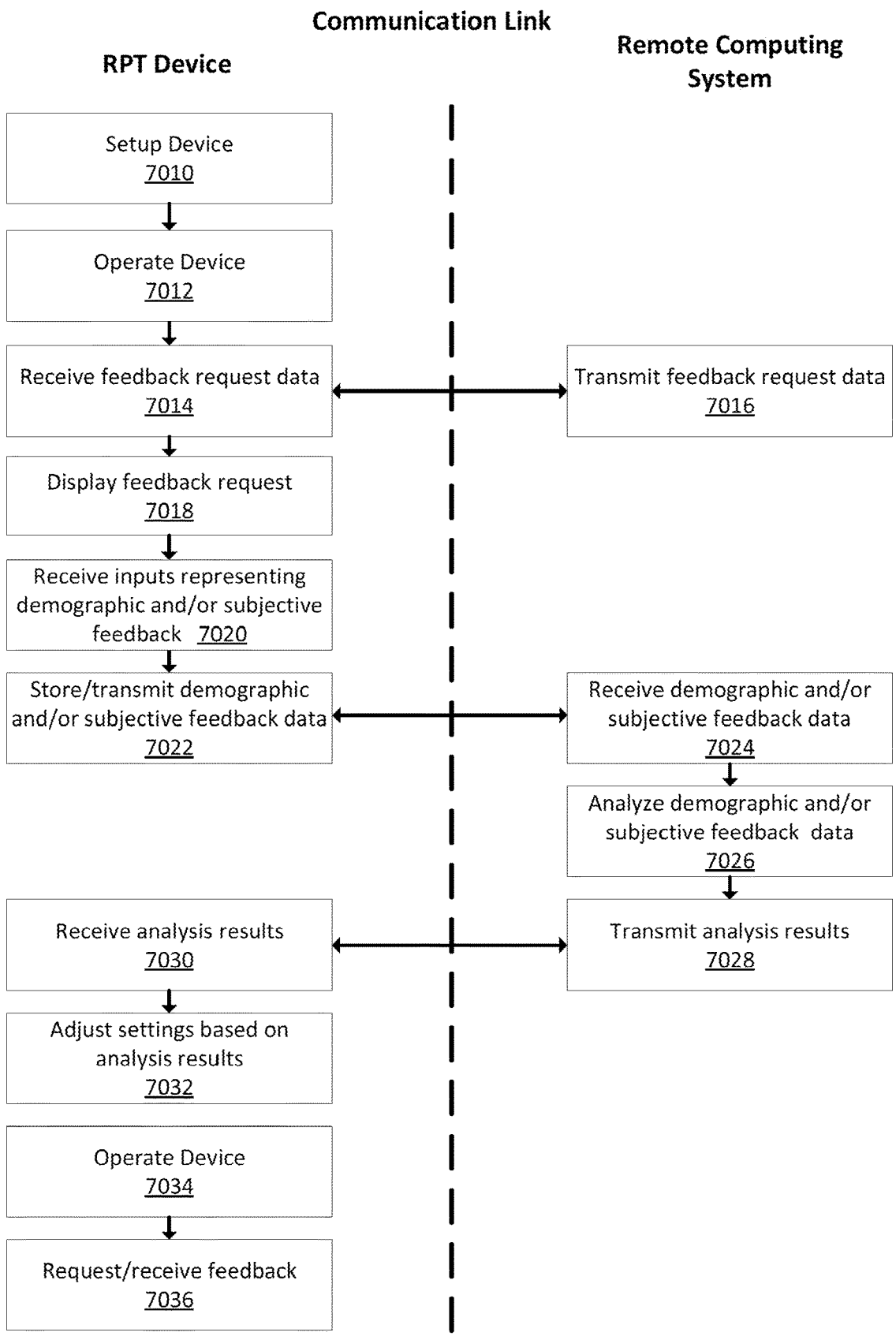

FIG. 4J shows another example of operations performed by an RPT device 4000 and a remote computing system. In the example, illustrated in FIG. 4H, the feedback request data was pre-stored on the RPT device 4000. For example, feedback request data may have been pre-stored in memory by the manufacturer, distributer or clinician. In the example illustrated in FIG. 4J, the remote computing system transmits the feedback request data (step 7016). The RPT device 4000 receives the transmitted feedback request data (step 7014) from the remote computing system and uses the data to receive feedback from the patient. In some examples, the system transmitting the feedback request data may be a different system from the system performing the analysis using the demographic and/or subjective feedback data transmitted from the RPT device 4000.

The remote computing system may transmit the feedback request data in response to a request form the RPT device 4000. In some examples, the remote computing system may push the feedback request data to the RPT device 4000 at some predetermined period of time, or ad hoc (either directly or through the home medical equipment).

The feedback request data may be entered by a physician or clinician. The physician or clinician may be provided with a user interface to enter their own questions as part of the feedback request data. The physician or clinician may be provided with a feature to ask their own patient questions via the RPT device 4000 or device associated with the RPT device 4000 (e.g., the local external device 4288). For example, the physician or clinician may enter the questions using the remote computing system. The physician or clinician may associate one or more of the questions with one or more conditions for distributing the questions to the RPT device 4000. The conditions may include one or more patient characteristics, device type, peripheral devices (e.g., type of mask, tube etc.) connected to the RPT device 4000, and/or device operating parameters.

Figure 4K:
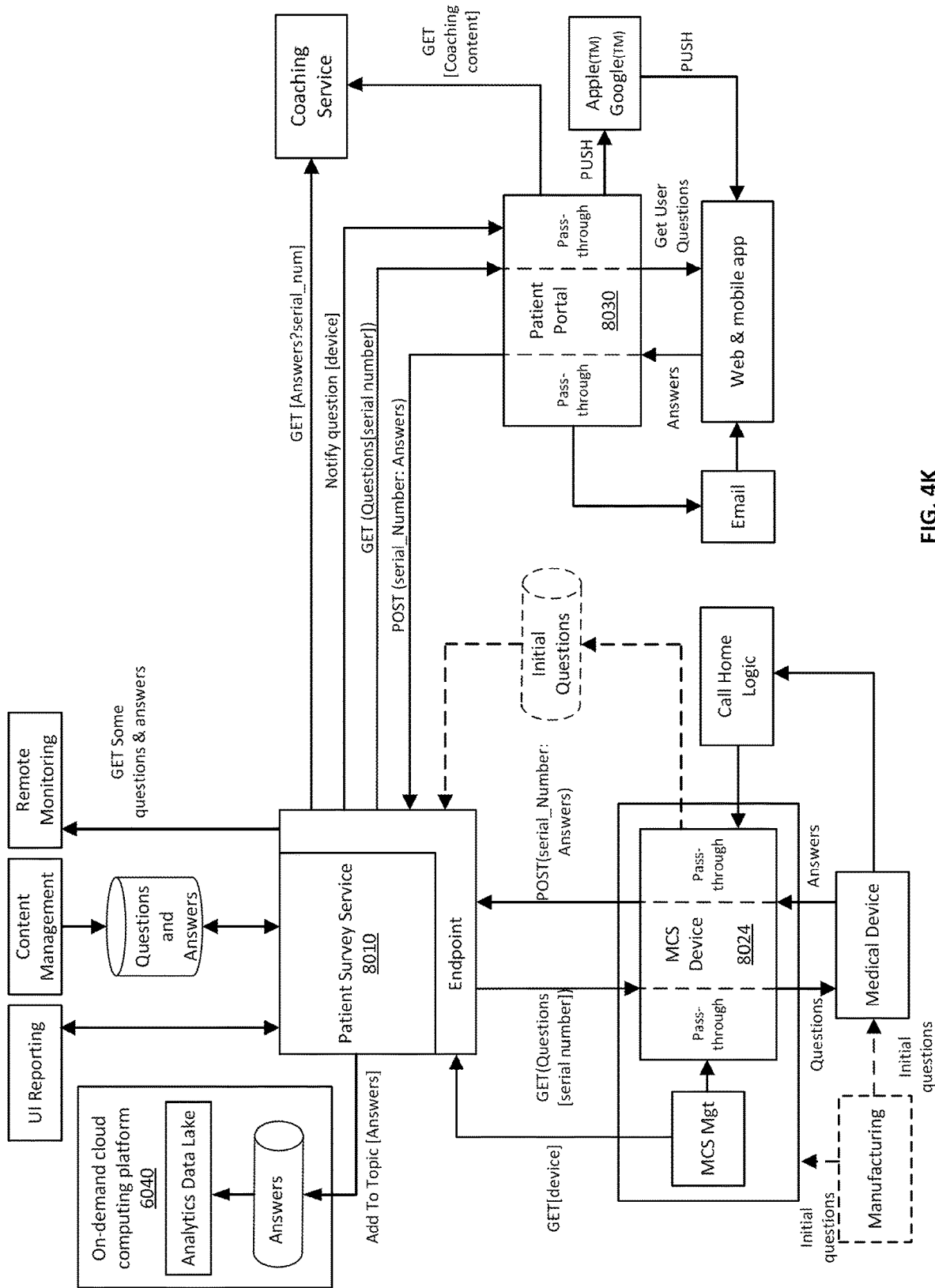

FIG. 4K shows a data flow diagram in a system providing communication between a medical device (e.g., RPT device 4000), a patient portal 8030 and a patient survey service 8010.

The patient survey service 8010 may be implemented on one or more servers which may include cloud and/or dedicated servers (e.g., server 6030). The patient survey service 8010 may coordinate the management and communication of questions and answers for the demographic and subjective feedback. As shown in FIG. 4K, the patient survey service 8010 may support sending questions to a patient's account associated with a medical device. The patient's account may be accessed via a web application or mobile application executed on a local device 4288 or via the RPT device 4000. The patient's account accessed via the web or mobile application can provide for monitoring, reporting and/or setting of the medical device, and coaching to the patient.

The patient survey service 8020 may notify clients of questions being available. The questions may be made available when they are added (e.g., by marketing) to a content management system. The questions may be retrieved from the patient survey service 8020 via GET calls. In one example, the patient's account accessed via the web or mobile application may call home and get questions via proxy through the patient portal 8030. The questions may be provided in JavaScript Object Notation (JSON) format, representing, the content of the questions and possible answers. The presentation of the questions may be embedded in the application as HTML content. The patient's account accessed via the web or mobile application may send answers back to the patient survey service 8020 via proxy through the patient portal 8030 (e.g., via a POST instruction).

The medical device may call home and get questions via proxy through the MCS device 8024 and send answer back to the patient survey service 8020 via proxy through the MCS device 8024 (e.g., via a POST instruction). The GET calls may include a serial number of the medical device for the patient survey service 8010 to keep track of which questions have been sent to which device and/or application.

According to one aspect, the patient survey service 8010 may manage the questions such that questions are made available to the patient portal after a predetermined period of time (e.g., 48 hours). This may minimize the questions being asked twice.

According to another aspect, the patient survey service 8010 may manage the questions such that questions already answered by a patient are not shown again. In one example, the patient survey service 8010 may keep track of answered questions on one platform (e.g., a medical device) and not display those questions on a patient's account accessed via a web or mobile application.

Responses to the questions may be received by the patient survey service 8010 from the medical device or the patient's account accessed via the web or mobile application. The answers may be transmitted to a cloud computing platform 6040 for advanced analytics. The cloud computing platform may include an analytics data lake with data from a large number of other patients. Deep neural networks may be used to build models and analyse the received answers. In some examples, the patient survey service 8010 may put the received answers on a queue for advance analytics consumption.

The patient survey service 8010 may support providing the questions and/or answers to a remote patient monitoring system. The remote monitoring may be provided via a web or mobile application executing on a remote external device 4286. The remote monitoring may provide for a secure, cloud-based patient management system for online patient monitoring, and enable clinician quick access to patient data, share clinical insights with other health professionals and reduce costs related to patient follow-up. The remote monitoring may receive operation information of the medical device, compliance information, setting of the device, changes made to the settings of the device, questions presented to the patient, and/or answers received from the patient. The clinician may use the data provided by the remote monitoring to suggest further changes to the coaching programs and/or personalized therapy of the patient.

The patient survey service 8010 may support receiving initial hard coded questions from the medical device. During manufacturing, initial questions may be loaded to the medical device. The medical device may present the initial questions and receive responses to the questions during setup or when a predetermined condition is satisfied (e.g., after the medical device has been used for a predetermined period of time or after a predetermined period of time has passed after setup). The initial questions may be transmitted by the medical device to the patient survey service 8010 for distribution to the remote monitoring and/or the web or mobile application. In some examples, the initial questions may be made available via the web or mobile application if the initial questions have not been answered on the medical device. The patient survey service 8010 may keep track of which initial questions have been answered.

In some examples, the initial questions stored on the medical device may be separately provided to the patient survey service 8010 by the manufacturer. In this example, the patient survey service 8010 may receive identification of the medical device (e.g., serial number) and the initial questions that have been stored on the medical device. The initial questions stored on different medical device may depend on the type of device and/or features provided by the device.

The patient portal 8030 may receive coaching content to provide the patient with instructions on how to use the device, how to improve use of the device, and/or get better results from the device. The coaching service may provide coaching content based on analysis results of the patient's demographic and/or subjective feedback.

5.6.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.7 Humidifier

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

According to one arrangement, the reservoir 5110 comprises a conductive portion 5120 configured to allow efficient transfer of heat from the heating element 5240 to the volume of liquid in the reservoir 5110, a humidifier reservoir dock 5130 (as shown in FIG. 5B) configured to receive the humidifier reservoir 5110 with a locking lever 5135 configured to retain the reservoir 5110 and/or a water level indicator 5150 (as shown in FIG. 5A-5B), and/or one or more humidifier transducers (sensors) 5210 instead of, or in addition to, transducers 4270 described above. The humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

Examples of the humidifier components are described in PCT application PCT/AU2014/050426 (WO2015089582), which is incorporated herein by reference.

5.8 Respiratory Pressure Therapy Modes

Various respiratory pressure therapy modes may be implemented by the RPT device 4000 depending on the values of the parameters A and $P_0$ in the treatment pressure equation Pt=$A\Pi\Phi$,t+$P_0$ used by the therapy parameter determination algorithm 4329 in one form of the present technology.

5.8.1 CPAP Therapy

In some implementations of this form of the present technology, the amplitude A is identically zero, so the treatment pressure Pt is identically equal to the base pressure $P_0$ throughout the respiratory cycle. Such implementations are generally grouped under the heading of CPAP therapy. In such implementations, there is no need for the therapy engine module 4320 to determine phase $\Phi$ or the waveform template $\Pi(\Phi)$. At step 4560, the central controller 4230 decreases the base pressure $P_0$ by a decrement, provided the decreased base pressure $P_0$ would not fall below a minimum treatment pressure Pmin. The method 4500 then returns to step 4520. In one implementation, the decrement is proportional to the value of $P_0$-Pmin, so that the decrease in $P_0$ to the minimum treatment pressure Pmin in the absence of any detected events is exponential. In one implementation, the constant of proportionality is set such that the time constant $\tau$ of the exponential decrease of $P_0$ is 60 minutes, and the minimum treatment pressure Pmin is 4 cmH$_2$O. In other implementations, the time constant $\tau$ could be as low as 1 minute and as high as 300 minutes, or as low as 5 minutes and as high as 180 minutes. In other implementations, the minimum treatment pressure Pmin can be as low as 0 cmH$_2$O and as high as 8 cmH$_2$O, or as low as 2 cmH$_2$O and as high as 6 cmH$_2$O. Alternatively, the decrement in $P_0$ could be predetermined, so the decrease in $P_0$ to the minimum treatment pressure Pmin in the absence of any detected events is linear.

5.8.2 Bi-Level Therapy

In other implementations of this form of the present technology, the value of amplitude A in equation Pt=$A\Pi\Phi$,t+$P_0$ may be positive. Such implementations are known as bi-level therapy, because in determining the treatment pressure Pt using equation Pt=$A\Pi\Phi$,t+$P_0$ with positive amplitude A, the therapy parameter determination algorithm 4329 oscillates the treatment pressure Pt between two values or levels in synchrony with the spontaneous respiratory effort of the patient 1000. That is, based on the typical waveform templates $\Pi(\Phi, t)$ described above, the therapy parameter determination algorithm 4329 increases the treatment pressure Pt to $P_0$+A (known as the IPAP) at the start of, or during, or inspiration and decreases the treatment pressure Pt to the base pressure $P_0$ (known as the EPAP) at the start of, or during, expiration.

In some forms of bi-level therapy, the IPAP is a treatment pressure that has the same purpose as the treatment pressure in CPAP therapy modes, and the EPAP is the IPAP minus the amplitude A, which has a "small" value (a few cmH$_2$O) sometimes referred to as the Expiratory Pressure Relief (EPR). Such forms are sometimes referred to as CPAP therapy with EPR, which is generally thought to be more comfortable than straight CPAP therapy. In CPAP therapy with EPR, either or both of the IPAP and the EPAP may be constant values that are hard-coded or manually entered to the RPT device 4000. Alternatively, the therapy parameter determination algorithm 4329 may repeatedly compute the IPAP and/or the EPAP during CPAP with EPR. In this alternative, the therapy parameter determination algorithm 4329 repeatedly computes the EPAP and/or the IPAP as a function of indices or measures of sleep disordered breathing returned by the respective algorithms in the therapy engine module 4320 in analogous fashion to the computation of the base pressure $P_0$ in APAP therapy described above.

In other forms of bi-level therapy, the amplitude A is large enough that the RPT device 4000 does some or all of the work of breathing of the patient 1000. In such forms, known as pressure support ventilation therapy, the amplitude A is referred to as the pressure support, or swing. In pressure support ventilation therapy, the IPAP is the base pressure $P_0$ plus the pressure support A, and the EPAP is the base pressure $P_0$.

In some forms of pressure support ventilation therapy, known as fixed pressure support ventilation therapy, the pressure support A is fixed at a predetermined value, e.g. 10 cmH$_2$O. The predetermined pressure support value is a setting of the RPT device 4000, and may be set for example by hard-coding during configuration of the RPT device 4000 or by manual entry through the input device 4220.

In other forms of pressure support ventilation therapy, broadly known as servo-ventilation, the therapy parameter determination algorithm 4329 takes as input some currently measured or estimated parameter of the respiratory cycle (e.g. the current measure Vent of ventilation) and a target value of that respiratory parameter (e.g. a target value Vtgt of ventilation) and repeatedly adjusts the parameters of equation Pt=$A\Pi\Phi$,t+$P_0$ to bring the current measure of the respiratory parameter towards the target value. In a form of servo-ventilation known as adaptive servo-ventilation (ASV), which has been used to treat CSR, the respiratory parameter is ventilation, and the target ventilation value Vtgt is computed by the target ventilation determination algorithm 4328 from the typical recent ventilation Vtyp, as described above.

In some forms of servo-ventilation, the therapy parameter determination algorithm 4329 applies a control methodology to repeatedly compute the pressure support A so as to bring the current measure of the respiratory parameter towards the target value. One such control methodology is Proportional-Integral (PI) control. In one implementation of PI control, suitable for ASV modes in which a target ventilation Vtgt is set to slightly less than the typical recent ventilation Vtyp, the pressure support A is repeatedly computed as:

$$A = G\int(\text{Vent} - \text{Vtgt})dt \qquad (1)$$

where G is the gain of the PI control. Larger values of gain G can result in positive feedback in the therapy engine module 4320. Smaller values of gain G may permit some residual untreated CSR or central sleep apnea. In some implementations, the gain G is fixed at a predetermined value, such as −0.4 cmH$_2$O/(L/min)/sec. Alternatively, the gain G may be varied between therapy sessions, starting small and increasing from session to session until a value that substantially eliminates CSR is reached. Conventional means for retrospectively analysing the parameters of a therapy session to assess the severity of CSR during the therapy session may be employed in such implementations In yet other implementations, the gain G may vary depending on the difference between the current measure Vent of ventilation and the target ventilation Vtgt.

Other servo-ventilation control methodologies that may be applied by the therapy parameter determination algorithm 4329 include proportional (P), proportional-differential (PD), and proportional-integral-differential (PID).

The value of the pressure support A computed via equation may be clipped to a range defined as [Amin, Amax]. In this implementation, the pressure support A sits by default at the minimum pressure support Amin until the measure of current ventilation Vent falls below the target ventilation Vtgt, at which point A starts increasing, only falling back to Amin when Vent exceeds Vtgt once again.

The pressure support limits Amin and Amax are settings of the RPT device 4000, set for example by hard-coding during configuration of the RPT device 4000 or by manual entry through the input device 4220.

In pressure support ventilation therapy modes, the EPAP is the base pressure $P_0$. As with the base pressure $P_0$ in CPAP therapy, the EPAP may be a constant value that is prescribed or determined during titration. Such a constant EPAP may be set for example by hard-coding during configuration of the RPT device 4000 or by manual entry through the input device 4220. This alternative is sometimes referred to as fixed-EPAP pressure support ventilation therapy. Titration of the EPAP for a given patient may be performed by a clinician during a titration session with the aid of PSG, with the aim of preventing obstructive apneas, thereby maintaining an open airway for the pressure support ventilation therapy, in similar fashion to titration of the base pressure $P_0$ in constant CPAP therapy.

Alternatively, the therapy parameter determination algorithm 4329 may repeatedly compute the base pressure $P_0$ during pressure support ventilation therapy. In such implementations, the therapy parameter determination algorithm 4329 repeatedly computes the EPAP as a function of indices or measures of sleep disordered breathing returned by the respective algorithms in the therapy engine module 4320, such as one or more of flow limitation, apnea, hypopnea, patency, and snore. Because the continuous computation of the EPAP resembles the manual adjustment of the EPAP by a clinician during titration of the EPAP, this process is also sometimes referred to as auto-titration of the EPAP, and the therapy mode is known as auto-titrating EPAP pressure support ventilation therapy, or auto-EPAP pressure support ventilation therapy.

5.9 Glossary

For the purposes of the present technology disclosure, in certain forms of the present technology, one or more of the following definitions may apply. In other forms of the present technology, alternative definitions may apply.

5.9.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.9.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.10 Other Remarks

A portion of the disclosure of this patent document contains material which is subject to copyright protection.

The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.11 Reference Signs List patient 1000
other patient 1002
other patient 1004
bed partner 1100
patient interface 3000
RPT device 4000
external housing 4010
upper portion 4012
portion 4014
panel(s) 4015
chassis 4016
handle 4018
pneumatic block 4020
air filter 4110
inlet air filter 4112
outlet air filter 4114
muffler 4120
inlet muffler 4122
outlet muffler 4124
pressure generator 4140
blower 4142
motor 4144
anti-spill back valve 4160
air circuit 4170
air circuit 4171
supplemental oxygen 4180
electrical components 4200
Single Printed Circuit Board Assembly 4202
power supply 4210
input device 4220
central controller 4230
clock 4232
therapy device controller 4240
protection circuits 4250
memory 4260
transducer 4270
pressure sensor 4272
flow sensor 4274
speed sensor 4276
data communication interface 4280
remote external communication network 4282
local external communication network 4284
remote external device 4286
local external device 4288
output device 4290 display driver 4292
display 4294
algorithms 4300
pre-processing module 4310
pressure compensation algorithm 4312
vent flow rate estimation 4314
leak flow rate estimation 4316
leak flow rate estimation 4316
respiratory flow rate estimation 4318
therapy engine module 4320
phase determination algorithm 4321
waveform determination algorithm 4322
ventilation determination algorithm 4323
inspiratory flow limitation determination algorithm 4324
apnea/hypopnea determination algorithm 4325
snore determination algorithm 4326
snore determination algorithm 4326
snore determination algorithms 4326
airway patency determination algorithm 4327
target ventilation determination algorithm 4328
therapy parameter determination algorithm 4329
therapy control module 4330
algorithm 4340
method 4500
step 4520
step 4560
humidifier 5000
humidifier inlet 5002
humidifier outlet 5004
humidifier base 5006
reservoir 5110
conductive portion 5120
humidifier reservoir dock 5130
locking lever 5135
water level indicator 5150
humidifier transducer 5210
pressure transducers 5212
flow rate transducers 5214
temperature transducers 5216
humidity sensor 5218
heating element 5240
humidifier controller 5250
central humidifier controller 5251
heating element controller 5252
air circuit controller 5254
remote external device 5286
communication link 6020
server 6030
cloud computing platform 6040
medical devices 6062
medical devices 6064
setup step 7010
step 7012
step 7014
step 7016
step 7018
step 7020
step 7022
step 7024
step 7026
step 7028
step 7030
step 7032
step 7034
step 7036
display screen 7050
display screen 7052
display screen 7054
display screen 7056
display screen 7058
display screen 7060
display screen 7062
display screen 7064
patient survey service 8010
patient survey service 8020
MCS device 8024
patient portal 8030

The invention claimed is:

1. A processing system comprising:
  memory storing a plurality of demographic questions and a plurality of subjective questions;
  a computing system including at least one hardware processor coupled to the memory, the computing system configured to:
    transmit, to a medical device associated with a patient, at least one demographic question and at least one subjective question stored in the memory;
    receive, from the medical device, answers to the at least one demographic question and at least one subjective question transmitted to the medical device;
    transmit, to a mobile device configured to execute an application for communicating with the medical device, a notification indicating that unanswered questions are available from among the plurality of demographic questions and the plurality of subjective questions stored in the memory;
    after transmitting the notifications, receive, from the mobile device, a request for the unanswered questions;
    responsive to the request, transmit, to the mobile device, a plurality of demographic questions and at least one subjective question from among the unanswered questions stored in the memory, the plurality of subjective questions transmitted to the mobile device including at least one question relating to subjective feedback for comfort level in using the medical device and at least one question relating to subjective feedback for sleep satisfaction when using the medical device;
    receive, from the mobile device, answers to the at least one demographic question and the plurality of subjective questions transmitted to the mobile device, wherein at least one of the answers to the subjective questions provides an input indicated on a varying scale between two responses; and
    perform advanced analytics to determine, based on (1) the answers received from the medical device and the mobile device and (2) answers received from a plurality of other medical devices, a tailored coaching program for the patient and personalised therapy using the medical device.

2. The processing system of claim 1, wherein the medical device is a respiratory treatment apparatus.

3. The processing system of claim 1, wherein the computing system is further configured to receive, from the medical device, answers to additional questions pre-stored on the medical device and answered using the medical device.

4. The processing system of claim 1, wherein the unanswered questions are transmitted to the mobile device after a predetermined condition is satisfied and/or the at least one demographic question and the at least one subjective question are transmitted to the medical device after the predetermined condition is satisfied.

5. The processing system of claim 4, wherein the predetermined condition is a predetermined time period after the medical device is setup and/or a predetermined time period that the medical device has been operated by the patient.

6. A processing system comprising:
memory storing a plurality of demographic questions for a patient using a medical device and a plurality of subjective questions relating to use of the medical device;
a computing system including at least one hardware processor coupled to the memory, the computing system configured to:
receive, from the medical device, answers to questions pre-stored on the medical device and answered by the patient via a user interface of the medical device before initial use of the medical device;
transmit, to the medical device associated with the patient, at least one demographic question from among the plurality of demographic questions stored in the memory and at least one subjective question from among the plurality of subjective questions stored in the memory;
in response to transmitting the at least one demographic question and the at least one subjective questions, receive, from the medical device, answers to the at least one demographic question and at least one subjective question transmitted to the medical device and answered by the patient via the user interface of the medical device;
transmit, to a mobile device configured to execute an application for communicating with the medical device, a notification indicating that unanswered demographic and subjective questions are available from among the plurality of demographic questions and the plurality of subjective questions stored in the memory;
after transmitting the notification, receive, from the mobile device, a request for the unanswered demographic and subjective questions;
responsive to the request, transmit, to the mobile device, at least one demographic question and a plurality of subjective questions from among the unanswered demographic and subjective questions stored in the memory, the plurality of subjective questions transmitted to the mobile device including at least one question relating to subjective feedback for comfort level in using the medical device and at least one question relating to subjective feedback for sleep satisfaction when using the medical device;
receive, from the mobile device, answers to the at least one demographic question and the at least one subjective question from among the unanswered questions transmitted to the mobile device and answered by the patient via a user interface of the mobile deice, wherein at least one of the answers to the at least one subjective question provides an input indicated on a varying scale between two responses to the at least one subject question;
receive answers from a plurality of other medical devices associated with other patients;
perform advanced analytics to determine, based on the answers received from the medical device, the answers received from the mobile device, and the answers received from the plurality of other medical devices associated with the other patients, a tailored coaching program for the patient using the medical device associated the patient and personalised therapy for setting operating parameters of the medical device associated the patient; and
transmit the tailored coaching program and the personalised therapy to the medical device.

7. The processing system of claim 6, wherein the medical device is a respiratory treatment apparatus.

8. The processing system of claim 6, wherein the unanswered demographic and subjective questions are transmitted to the mobile device after a predetermined condition is satisfied.

9. The processing system of claim 8, wherein the predetermined condition is a predetermined time period after the medical device is setup and/or a predetermined time period that the medical device has been operated by the patient.

10. The processing system of claim 6, wherein the at least one demographic question and the at least one subjective question are transmitted to the medical device after a predetermined condition is satisfied.

11. The processing system of claim 10, wherein the predetermined condition is a predetermined time period after the medical device is setup and/or a predetermined time period that the medical device has been operated by the patient.

12. The processing system of claim 6, wherein each of the plurality of subjective questions stored in the memory is associated with one or more conditions for distributing the corresponding question from the among the plurality of subjective questions to the medical device.

13. The processing system of claim 12, wherein the one or more conditions include one or more patient characteristics being satisfied based on the answers to the questions pre-stored on the medical device.

14. The processing system of claim 12, wherein the one or more conditions include a specific type of peripheral device being connected to the medical device.

15. The processing system of claim 12, wherein the one or more conditions include specific operating parameters set for the medical device.

16. The processing system of claim 6, wherein the computing system is further configured to: transmit a message to the mobile device and the medical device indicating that the patient needs to schedule a meeting with a clinician, wherein transmitting the message is determined by the computing system based on answers, received from the mobile device, to the at least one demographic question and the at least one subjective question.

* * * * *